US011304837B2

(12) United States Patent
Eller et al.

(10) Patent No.: US 11,304,837 B2
(45) Date of Patent: *Apr. 19, 2022

(54) IMPLANTABLE DEVICE DELIVERY SYSTEM

(71) Applicant: Merit Medical System, Inc., South Jordan, UT (US)

(72) Inventors: Zeke Eller, Plano, TX (US); Thomas Patrick Robinson, Addison, TX (US); Barton Gill, South Jordan, UT (US); Darla Gill, Salt Lake City, UT (US); Bryan K. Elwood, Arlington, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 107 days.

This patent is subject to a terminal disclaimer.

(21) Appl. No.: 16/679,680

(22) Filed: Nov. 11, 2019

(65) Prior Publication Data
US 2020/0146860 A1 May 14, 2020

Related U.S. Application Data

(63) Continuation of application No. 15/263,741, filed on Sep. 13, 2016, now Pat. No. 10,470,906.
(Continued)

(51) Int. Cl.
*A61F 2/966* (2013.01)
*A61F 2/915* (2013.01)

(52) U.S. Cl.
CPC .............. *A61F 2/966* (2013.01); *A61F 2/915* (2013.01); *A61F 2002/9665* (2013.01)

(58) Field of Classification Search
CPC ... A61F 2/966; A61F 2/915; A61F 2002/9665
See application file for complete search history.

(56) References Cited

U.S. PATENT DOCUMENTS 4,913,141 A * 4/1990 Hillstead .................. A61F 2/88
606/194
5,201,757 A 4/1993 Heyn et al.
(Continued)

FOREIGN PATENT DOCUMENTS

DE 4323866 1/1994
EP 0364420 4/1990
(Continued)

OTHER PUBLICATIONS

Office Action dated Jan. 22, 2013 for U.S. Appl. No. 10/585,430.
(Continued)

*Primary Examiner* — Richard G Louis
(74) *Attorney, Agent, or Firm* — Stoel Rives LLP

(57) ABSTRACT

Delivery systems and methods for deploying an implantable device are disclosed, which can include a delivery device having an outer tubular member and an inner assembly. The inner assembly is disposed within and is slidably movable relative to the outer tubular member. The inner assembly can include a pusher at a distal portion. The pusher abuts and restricts proximal movement, relative to the inner assembly, of a crimped implantable device within the outer tubular member. The pusher can include a slot to accommodate a suture binding mechanism of the implantable device. The delivery device can include a tip disposed at a distal end. The tip includes a tip transition zone. The inner sheath and outer tubular member can each have sections of distinct rigidity along their lengths with transition zones between the sections. A transition zone of the outer tubular member and a transition zone of the inner sheath can be longitudinally offset.

20 Claims, 14 Drawing Sheets

Related U.S. Application Data

(60) Provisional application No. 62/218,892, filed on Sep. 15, 2015.

(56) References Cited

U.S. PATENT DOCUMENTS

| | | |
|---|---|---|
| 5,591,172 A | 1/1997 | Bachmann et al. |
| 5,591,196 A | 1/1997 | Marin et al. |
| 5,603,698 A | 2/1997 | Roberts et al. |
| 5,645,559 A | 7/1997 | Hachtman et al. |
| 5,733,325 A | 3/1998 | Robinson et al. |
| 5,755,769 A | 5/1998 | Richard et al. |
| 5,759,186 A | 6/1998 | Bachmann et al. |
| 5,824,041 A | 10/1998 | Lenker et al. |
| 5,868,755 A | 2/1999 | Kanner et al. |
| 5,876,448 A | 3/1999 | Thompson et al. |
| 5,916,147 A | 6/1999 | Boury |
| 5,968,052 A | 10/1999 | Sullivan, III et al. |
| 6,015,429 A | 1/2000 | Lau et al. |
| 6,093,194 A | 7/2000 | Mikus et al. |
| 6,123,715 A | 9/2000 | Amplatz |
| 6,143,021 A | 11/2000 | Staehle |
| 6,146,415 A | 11/2000 | Fitz |
| 6,162,231 A | 12/2000 | Mikus et al. |
| 6,241,757 B1 | 6/2001 | An et al. |
| 6,270,524 B1 | 8/2001 | Kim |
| 6,283,992 B1 | 9/2001 | Hankh et al. |
| 6,368,339 B1 | 4/2002 | Amplatz |
| 6,383,211 B1 | 5/2002 | Staehle |
| 6,391,051 B2 | 5/2002 | Sullivan, III et al. |
| 6,413,269 B1 | 7/2002 | Bui et al. |
| 6,416,545 B1 | 7/2002 | Mikus et al. |
| 6,428,566 B1 | 8/2002 | Holt |
| 6,443,980 B1 | 9/2002 | Wang et al. |
| 6,447,531 B1 | 9/2002 | Amplatz |
| 6,514,261 B1 | 2/2003 | Randall et al. |
| 6,530,933 B1 | 3/2003 | Yeung et al. |
| 6,599,296 B1 | 7/2003 | Gillick et al. |
| 6,599,308 B2 | 7/2003 | Amplatz |
| 6,613,079 B1 | 9/2003 | Wolinsky et al. |
| 6,616,675 B1 | 9/2003 | Evard et al. |
| 6,629,981 B2 | 10/2003 | Dennis et al. |
| 6,645,143 B2 | 11/2003 | Vantassel et al. |
| 6,669,719 B2 | 12/2003 | Wallace et al. |
| 6,726,712 B1 | 4/2004 | Raeder-Devens et al. |
| 6,746,480 B2 | 6/2004 | Scholz et al. |
| 6,770,101 B2 | 8/2004 | Desmond, III et al. |
| 6,776,791 B1 | 8/2004 | Jody et al. |
| 6,821,295 B1 | 11/2004 | Farrar |
| 6,866,669 B2 | 3/2005 | Buzzard et al. |
| 6,893,413 B2 | 5/2005 | Martin |
| 6,926,732 B2 | 8/2005 | Derus et al. |
| 6,955,685 B2 | 10/2005 | Escamilla et al. |
| 7,004,966 B2 | 2/2006 | Edwin et al. |
| 7,083,640 B2 | 8/2006 | Lombardi et al. |
| 7,309,350 B2 | 12/2007 | Landreville et al. |
| 7,309,351 B2 | 12/2007 | Escamilla et al. |
| 7,393,357 B2 | 7/2008 | Stelter et al. |
| 7,473,271 B2 | 1/2009 | Gunderson |
| 7,591,848 B2 | 9/2009 | Allen |
| 7,637,942 B2 | 12/2009 | Mangiardi et al. |
| 7,731,654 B2 | 6/2010 | Mangiardi et al. |
| 7,959,671 B2 | 6/2011 | Mangiardi et al. |
| 8,012,194 B2 | 9/2011 | Edwin et al. |
| 8,206,436 B2 | 6/2012 | Mangiardi et al. |
| 8,262,719 B2 | 9/2012 | Erickson et al. |
| 8,357,193 B2 | 1/2013 | Phan et al. |
| 8,414,635 B2 | 4/2013 | Hyodoh et al. |
| 8,425,539 B2 | 4/2013 | Binmoeller et al. |
| 8,439,934 B2 | 5/2013 | Satasiya et al. |
| 8,454,632 B2 | 6/2013 | Binmoeller et al. |
| 8,518,099 B2 | 8/2013 | Chanduszko et al. |
| 8,524,132 B2 | 9/2013 | Von Oepen et al. |
| 8,535,366 B2 | 9/2013 | Mangiardi et al. |
| 8,652,099 B2 | 2/2014 | Fierens et al. |
| 8,677,874 B2 | 3/2014 | Lilburn et al. |
| 8,696,611 B2 | 4/2014 | Yaacov et al. |
| 8,715,334 B2 | 5/2014 | Clerc et al. |
| 8,906,081 B2 | 12/2014 | Cully et al. |
| 8,926,683 B2 | 1/2015 | Darla et al. |
| 9,155,643 B2 | 10/2015 | Clerc et al. |
| 9,192,496 B2 | 11/2015 | Robinson |
| 9,259,336 B2 | 2/2016 | Schaeffer et al. |
| 9,284,637 B2 | 3/2016 | Boyle et al. |
| 9,381,041 B2 | 7/2016 | Brown et al. |
| 2001/0037141 A1 | 11/2001 | Yee et al. |
| 2002/0138095 A1 | 9/2002 | Mazzocchi et al. |
| 2002/0151967 A1 | 10/2002 | Mikus et al. |
| 2002/0183827 A1 | 12/2002 | Derus et al. |
| 2002/0193749 A1 | 12/2002 | Olovson |
| 2003/0023268 A1 | 1/2003 | Lizardi |
| 2003/0050686 A1 | 3/2003 | Raeder-Devens et al. |
| 2003/0135268 A1 | 7/2003 | Desai |
| 2003/0167060 A1 | 9/2003 | Buzzard et al. |
| 2004/0030381 A1 | 2/2004 | Shu |
| 2004/0193243 A1 | 9/2004 | Mangiardi et al. |
| 2004/0267281 A1 | 12/2004 | Harari et al. |
| 2005/0027345 A1 | 2/2005 | Horan et al. |
| 2005/0038495 A1 | 2/2005 | Greenan |
| 2005/0090887 A1 | 4/2005 | Pryor |
| 2005/0125050 A1 | 6/2005 | Carter et al. |
| 2005/0149160 A1 | 7/2005 | McFerran |
| 2005/0182475 A1* | 8/2005 | Jen .................. A61F 2/95 623/1.11 |
| 2005/0278010 A1 | 12/2005 | Richardson |
| 2005/0283179 A1* | 12/2005 | Lentz ............. A61M 25/0662 606/192 |
| 2006/0020321 A1 | 1/2006 | Parker |
| 2006/0155368 A1 | 7/2006 | Shin |
| 2006/0184224 A1 | 8/2006 | Angel |
| 2006/0258972 A1 | 11/2006 | Mangiardi et al. |
| 2007/0005122 A1 | 1/2007 | Inoue |
| 2007/0043421 A1 | 2/2007 | Mangiardi et al. |
| 2007/0100421 A1 | 5/2007 | Griffin |
| 2007/0135904 A1 | 6/2007 | Eidenschink et al. |
| 2007/0156225 A1 | 7/2007 | George et al. |
| 2007/0179590 A1 | 8/2007 | Lu et al. |
| 2007/0208350 A1 | 9/2007 | Gunderson |
| 2007/0250150 A1 | 10/2007 | Pal et al. |
| 2007/0270932 A1 | 11/2007 | Headley et al. |
| 2008/0114443 A1 | 5/2008 | Mitchell et al. |
| 2008/0140178 A1 | 6/2008 | Rasmussen et al. |
| 2008/0228256 A1 | 9/2008 | Erickson et al. |
| 2008/0288042 A1 | 11/2008 | Purdy et al. |
| 2009/0099636 A1 | 4/2009 | Chanduszko et al. |
| 2009/0099647 A1 | 4/2009 | Glimsdale et al. |
| 2009/0118740 A1 | 5/2009 | Mangiardi et al. |
| 2009/0157158 A1 | 6/2009 | Ondracek |
| 2009/0171427 A1 | 7/2009 | Melsheimer et al. |
| 2009/0187240 A1 | 7/2009 | Clerc |
| 2009/0192518 A1 | 7/2009 | Golden et al. |
| 2009/0292262 A1 | 11/2009 | Adams et al. |
| 2010/0023032 A1 | 1/2010 | Granja et al. |
| 2010/0023132 A1 | 1/2010 | Imran |
| 2010/0030256 A1 | 2/2010 | Dubrul et al. |
| 2010/0049295 A1 | 2/2010 | Satasiya et al. |
| 2010/0057145 A1 | 3/2010 | Bhatnagar et al. |
| 2010/0057185 A1 | 3/2010 | Melsheimer et al. |
| 2010/0145431 A1 | 6/2010 | Wu et al. |
| 2010/0252470 A1 | 10/2010 | Ryan et al. |
| 2011/0004290 A1 | 1/2011 | Bales, Jr. et al. |
| 2011/0015616 A1 | 1/2011 | Straubinger et al. |
| 2011/0082464 A1 | 4/2011 | Douk et al. |
| 2011/0190862 A1 | 8/2011 | Mehran et al. |
| 2011/0208296 A1 | 8/2011 | Duffy et al. |
| 2011/0264191 A1 | 10/2011 | Rothstein |
| 2011/0288482 A1 | 11/2011 | Farrell et al. |
| 2011/0307070 A1 | 12/2011 | Clerc et al. |
| 2011/0319980 A1 | 12/2011 | Ryan |
| 2012/0046729 A1 | 2/2012 | Von Oepen et al. |
| 2012/0095567 A1* | 4/2012 | Weisman ............. A61F 2/95 623/23.7 |
| 2012/0136426 A1 | 5/2012 | Phan et al. |
| 2012/0296257 A1 | 11/2012 | Van Dan et al. |

(56) References Cited

U.S. PATENT DOCUMENTS

| | | | |
|---|---|---|---|
| 2012/0303109 A1* | 11/2012 | Okuma | A61F 2/95 623/1.11 |
| 2012/0303112 A1 | 11/2012 | Armstrong et al. | |
| 2012/0310320 A1 | 12/2012 | Gill et al. | |
| 2013/0018215 A1 | 1/2013 | Snider et al. | |
| 2013/0110221 A1 | 5/2013 | Campbell et al. | |
| 2013/0116770 A1 | 5/2013 | Robinson | |
| 2013/0116771 A1 | 5/2013 | Robinson | |
| 2013/0116772 A1 | 5/2013 | Robinson et al. | |
| 2013/0158673 A1 | 6/2013 | Toomey | |
| 2013/0184833 A1 | 7/2013 | Ryan et al. | |
| 2013/0197623 A1 | 8/2013 | McHugo | |
| 2013/0231689 A1 | 9/2013 | Binmoeller et al. | |
| 2013/0253546 A1 | 9/2013 | Sander et al. | |
| 2013/0274870 A1 | 10/2013 | Lombardi et al. | |
| 2014/0074065 A1 | 3/2014 | Muni et al. | |
| 2014/0074219 A1 | 3/2014 | Hingston et al. | |
| 2014/0236064 A1 | 8/2014 | Binmoeller et al. | |
| 2014/0243992 A1 | 9/2014 | Walsh et al. | |
| 2014/0288636 A1 | 9/2014 | Headley, Jr. et al. | |
| 2014/0303709 A1 | 10/2014 | Dwork | |
| 2014/0330305 A1 | 11/2014 | Rood et al. | |
| 2014/0350694 A1 | 11/2014 | Behan | |
| 2014/0364959 A1 | 12/2014 | Attar et al. | |
| 2015/0100133 A1 | 4/2015 | Xie et al. | |
| 2015/0112377 A1 | 4/2015 | Arnone et al. | |
| 2015/0173919 A1 | 6/2015 | Baldwin | |
| 2015/0313595 A1 | 11/2015 | Houshton et al. | |
| 2015/0313599 A1 | 11/2015 | Johnson et al. | |
| 2016/0081823 A1 | 3/2016 | Majercak | |
| 2016/0081832 A1 | 3/2016 | Hingston et al. | |
| 2016/0242846 A1 | 8/2016 | Brown et al. | |
| 2017/0035424 A1 | 2/2017 | Binmoeller et al. | |
| 2017/0035426 A1 | 2/2017 | Phan et al. | |
| 2017/0035427 A1 | 2/2017 | Sander et al. | |
| 2017/0035428 A1 | 2/2017 | Binmoeller et al. | |
| 2018/0303594 A1 | 10/2018 | Eller et al. | |

FOREIGN PATENT DOCUMENTS

| | | |
|---|---|---|
| EP | 0408245 | 1/1991 |
| EP | 0872220 | 10/1998 |
| EP | 1637092 | 3/2006 |
| WO | 199631174 | 10/1996 |
| WO | 2000078246 | 12/2000 |
| WO | 2002087470 | 11/2002 |
| WO | 2003090644 | 11/2003 |
| WO | 2004030571 | 4/2004 |
| WO | 2005070095 | 8/2005 |
| WO | 2008042266 | 4/2008 |
| WO | 2010130297 | 11/2010 |
| WO | 2012062603 | 10/2012 |
| WO | 2013045262 | 4/2013 |
| WO | 2013066883 | 10/2013 |

OTHER PUBLICATIONS

Office Action dated Jan. 31, 2012 for U.S. Appl. No. 10/585,430.
Office Action dated Mar. 16, 2015 for U.S. Appl. No. 13/664,234.
Office Action dated Mar. 22, 2016 for U.S. Appl. No. 13/664,234.
Office Action dated Mar. 24, 2015 for U.S. Appl. No. 13/664,267.
Office Action dated Apr. 6, 2016 for U.S. Appl. No. 13/664,137.
Office Action dated Apr. 25, 2018 for U.S. Appl. No. 15/061,107.
Office Action dated May 5, 2014 for U.S. Appl. No. 13/313,929.
Office Action dated May 25, 2012 for U.S. Appl. No. 12/535,980.
Office Action dated May 30, 2019 for U.S. Appl. No. 15/263,741.
Office Action dated Jun. 7, 2011 for U.S. Appl. No. 10/585,430.
Office Action dated Jul. 9, 2009 for U.S. Appl. No. 11/432,964.
Office Action dated Jul. 25, 2013 for U.S. Appl. No. 11/432,964.
Office Action dated Aug. 13, 2012 for U.S. Appl. No. 10/585,430.
Office Action dated Sep. 19, 2018 for U.S. Appl. No. 15/061,107.
Office Action dated Oct. 7, 2015 for U.S. Appl. No. 13/664,234.
Office Action dated Oct. 16, 2015 for U.S. Appl. No. 13/664,267.
Office Action dated Oct. 16, 2017 for U.S. Appl. No. 15/061,107.
Office Action dated Nov. 9, 2010 for U.S. Appl. No. 10/585,430.
Office Action dated Nov. 14, 2012 for U.S. Appl. No. 12/535,980.
Office Action dated Nov. 14, 2018 for U.S. Appl. No. 15/263,741.
Office Action dated Nov. 19, 2015 for U.S. Appl. No. 13/664,137.
Office Action dated Nov. 30, 2016 for U.S. Appl. No. 13/664,137.
Office Action dated Dec. 7, 2009 for U.S. Appl. No. 11/432,964.
Office Action dated Dec. 8, 2009 for U.S. Appl. No. 10/585,430.
Sen, et al.,Laplace's Equation for Convective Scalar Transport in Potential Flow, Proc. R. Soc. Lond. A 456, pp. 3041-3045 ,2000.
European Examination Report dated Feb. 18, 2015 for EP09791142.4.
International Preliminary Report dated May 15, 2014 for PCT/US2012/062603.
International Publication and Search Report dated Jun. 14, 2012 for WO2012078794.
International Publication and Search Report dated Feb. 25, 2012 for WO2010021836.
International Publication and Search Report dated Aug. 4, 2005 for WO2005070095.
International Search Report and Written Opinion dated Jan. 9, 2018 for PCT/US2017/054000.
International Search Report and Written Opinion dated Mar. 16, 2012 for PCT/US2011/063799.
International Search Report and Written Opinion dated Mar. 29, 2013 for PCT/US2012/062603.
International Search Report and Written Opinion dated Jun. 22, 2016 for PCT/US2016/020900.
International Search Report and Written Opinion dated Jun. 29, 2018 for PCT/US2018/022344.
International Search Report and Written Opinion dated Aug. 2, 2018 for PCT/US2018/028107.
International Search Report and Written Opinion dated Sep. 28, 2005 for PCT/US2005/000515.
International Search Report and Written Opinion dated Oct. 29, 2009 for PCT/US2009/052691.
International Search Report and Written Opinion dated Nov. 23, 2006 for PCT/US2006/018811.
Notice of Allowance dated Jan. 14, 2015 for U.S. Appl. No. 11/432,964.
Notice of Allowance dated Feb. 25, 2019 for U.S. Appl. No. 15/061,107.
Notice of Allowance dated Mar. 6, 2013 for U.S. Appl. No. 12/535,980.
Notice of Allowance dated Jun. 11, 2013 for U.S. Appl. No. 10/585,430.
Notice of Allowance dated Jun. 22, 2016 for U.S. Appl. No. 13/664,267.
Notice of Allowance dated Aug. 12, 2015 for U.S. Appl. No. 13/664,200.
Notice of Allowance dated Sep. 6, 2018 for U.S. Appl. No. 29/597,873.
Notice of Allowance dated Sep. 11, 2019 for U.S. Appl. No. 15/263,741.
Notice of Allowance dated Sep. 23, 2016 for U.S. Appl. No. 13/664,234.
Notice of Allowance dated Oct. 21, 2014 for U.S. Appl. No. 13/313,929.
Office Action dated Jan. 3, 2014 for U.S. Appl. No. 11/432,964.
European Examination Report dated Apr. 26, 2021 for EP11846358.7.

* cited by examiner

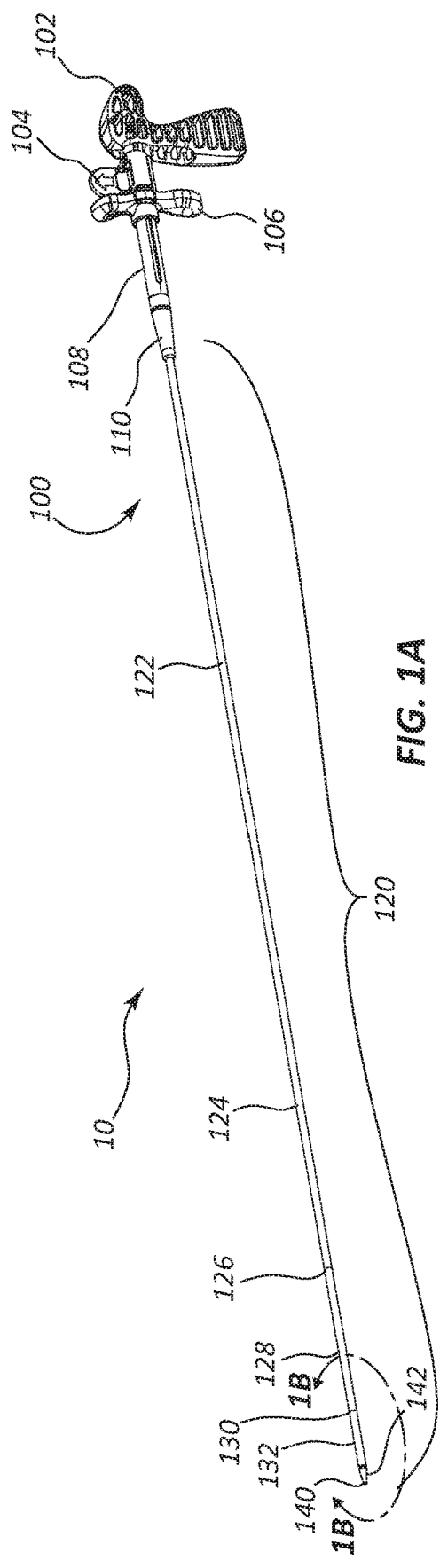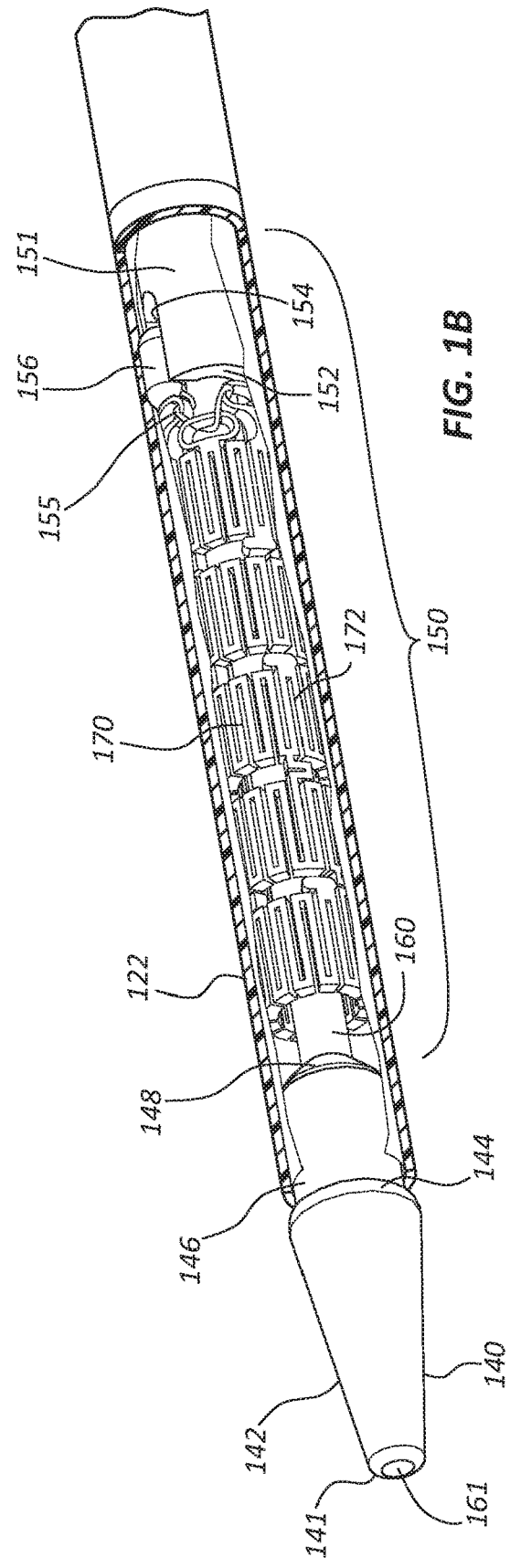

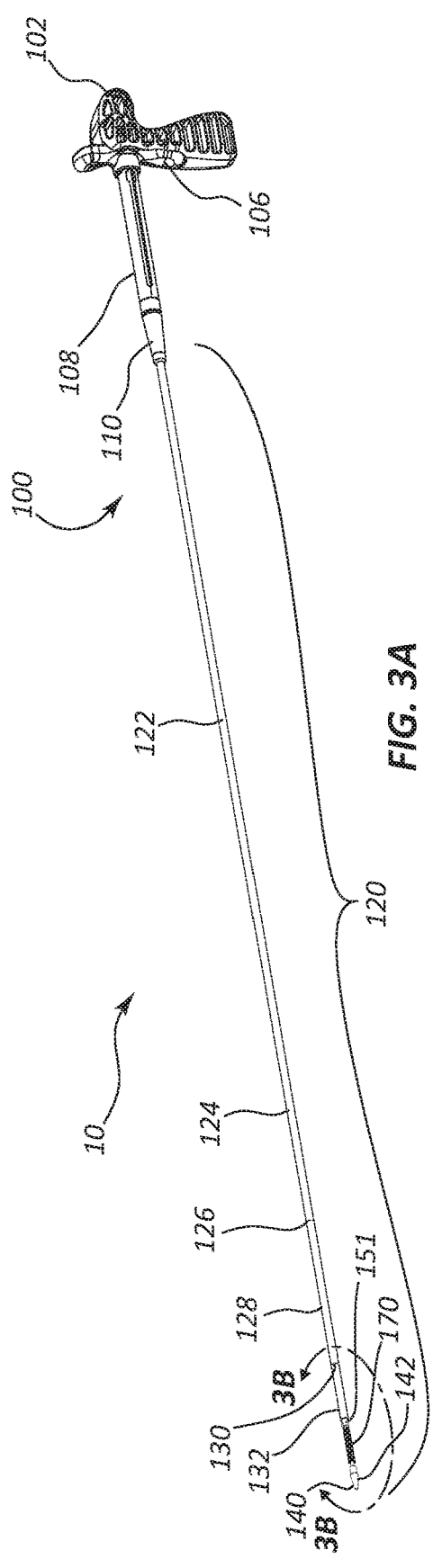
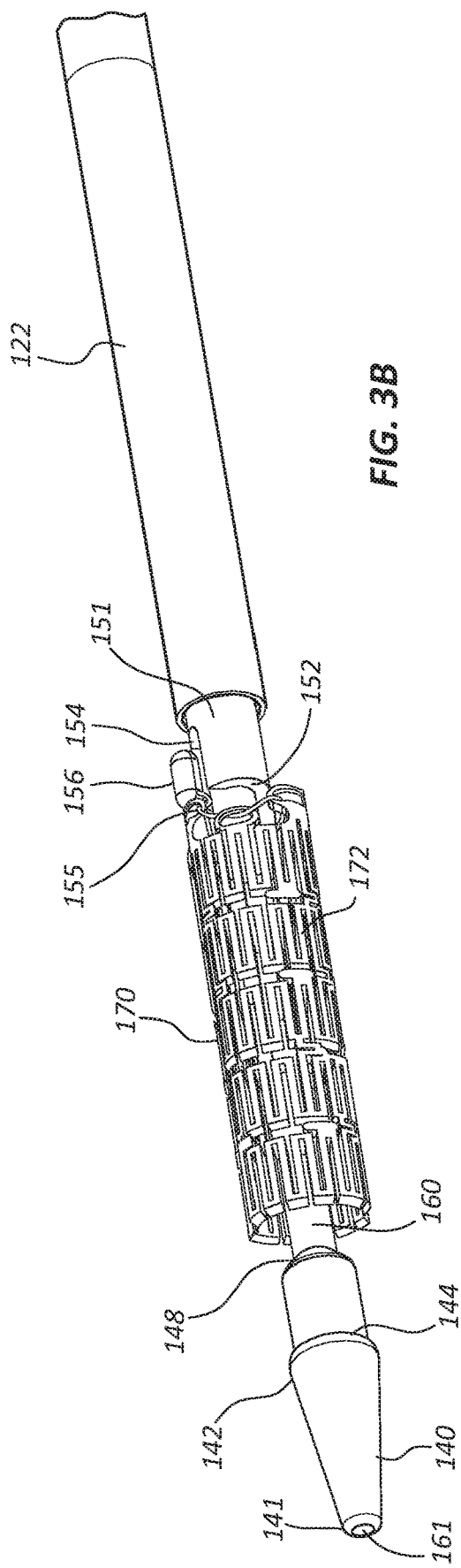
FIG. 3A
FIG. 3B

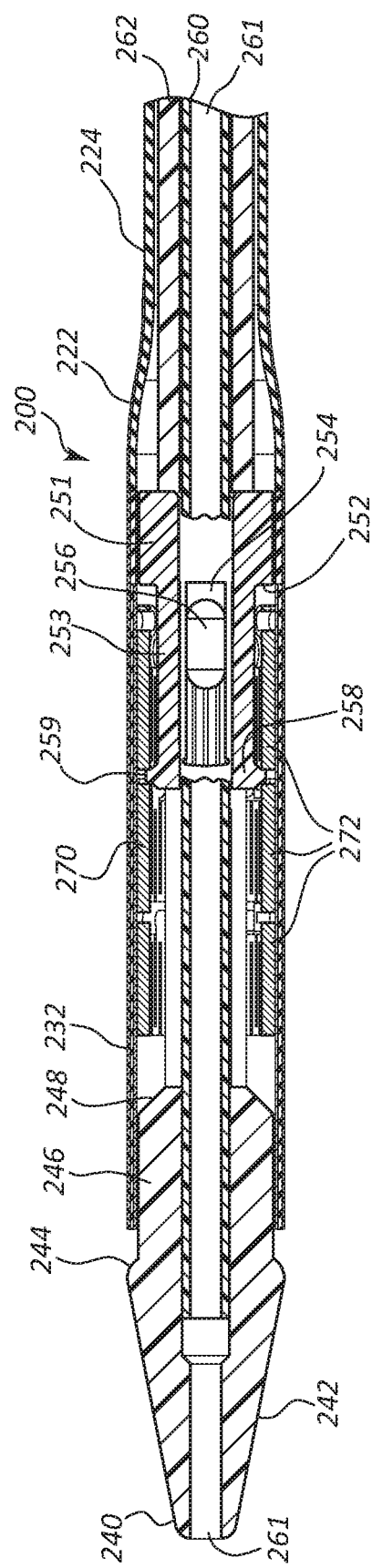
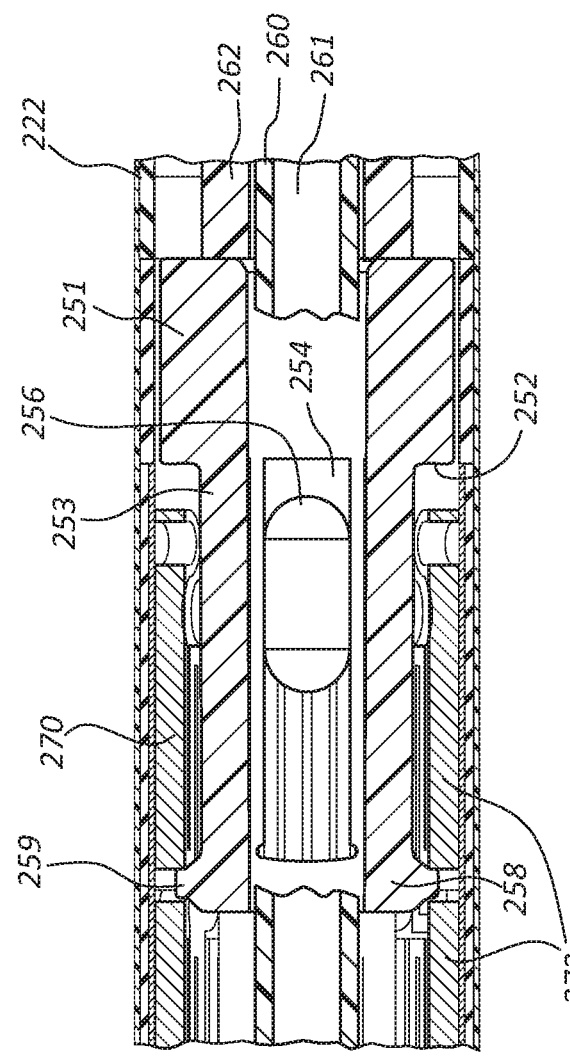

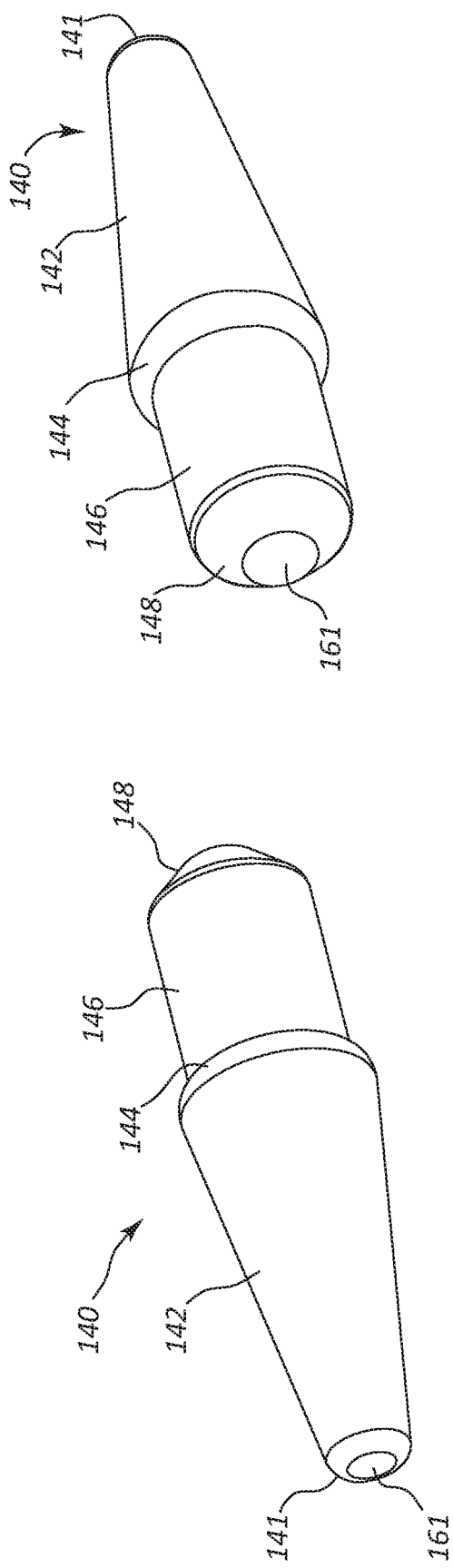
FIG. 7A
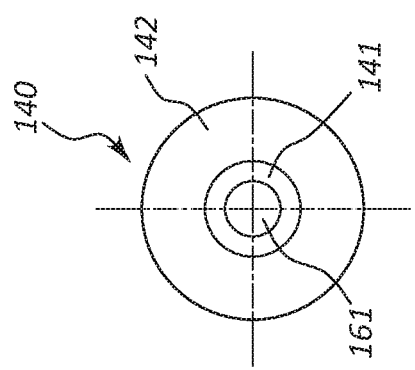
FIG. 7B
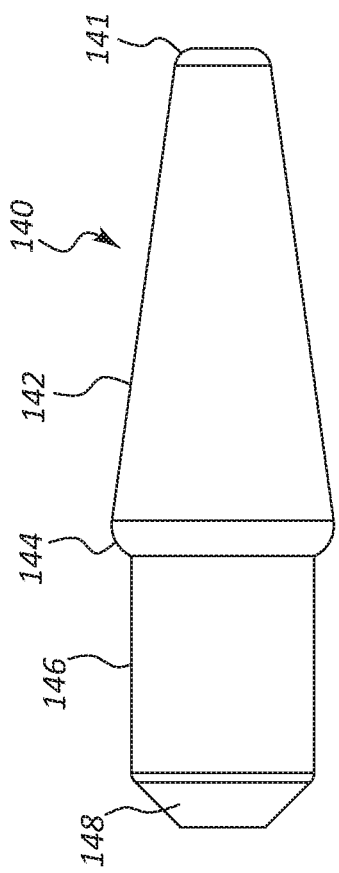
FIG. 7C
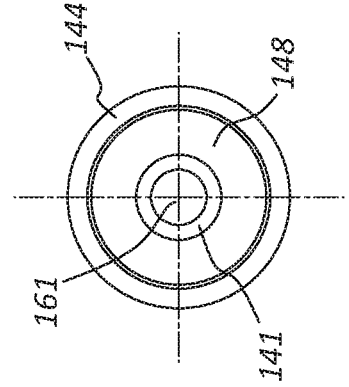
FIG. 7D
FIG. 7E

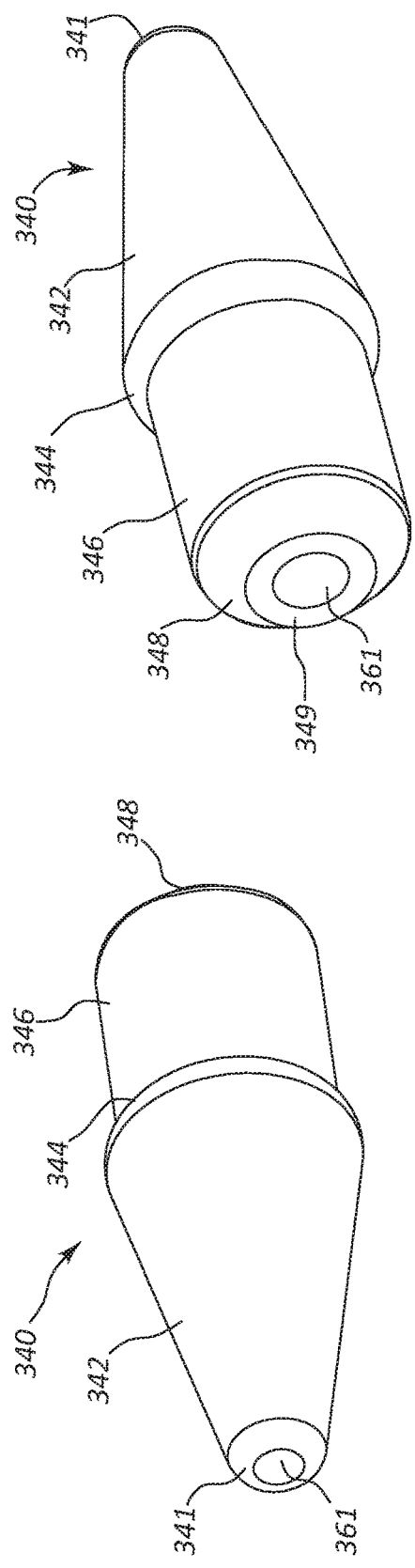
FIG. 8A
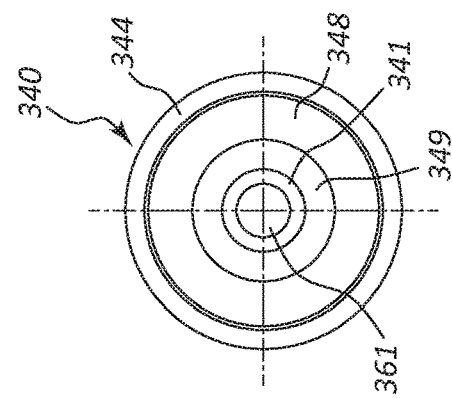
FIG. 8B
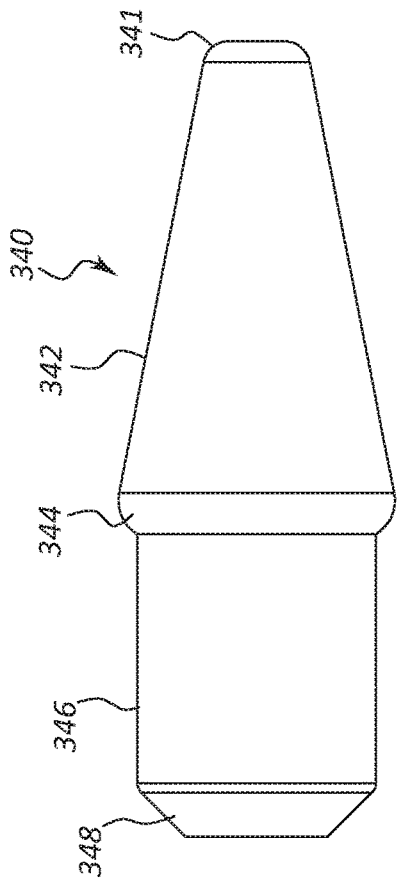
FIG. 8C
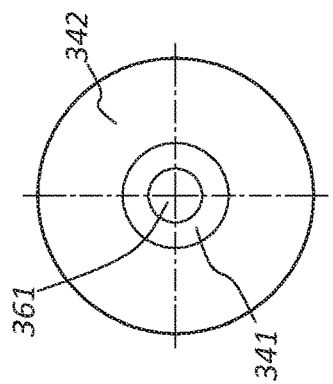
FIG. 8D
FIG. 8E

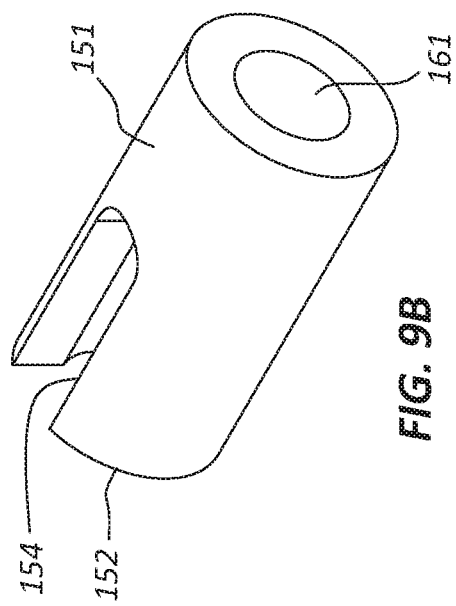
FIG. 9B
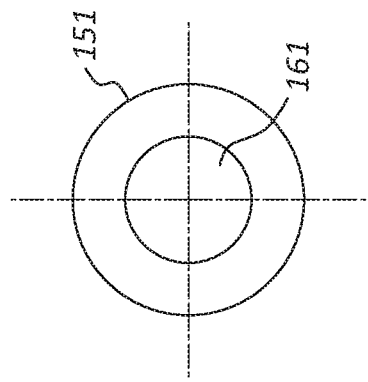
FIG. 9G
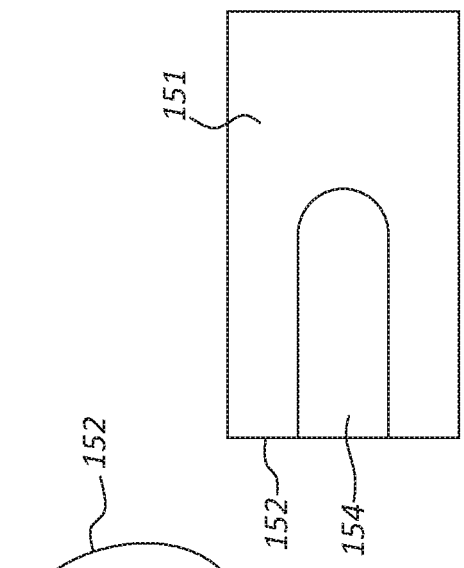
FIG. 9A
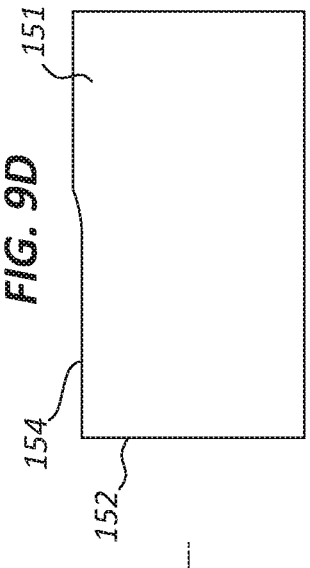
FIG. 9D
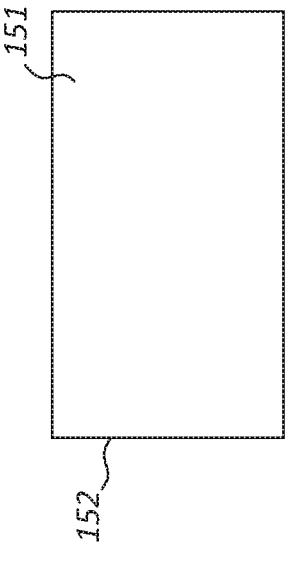
FIG. 9C
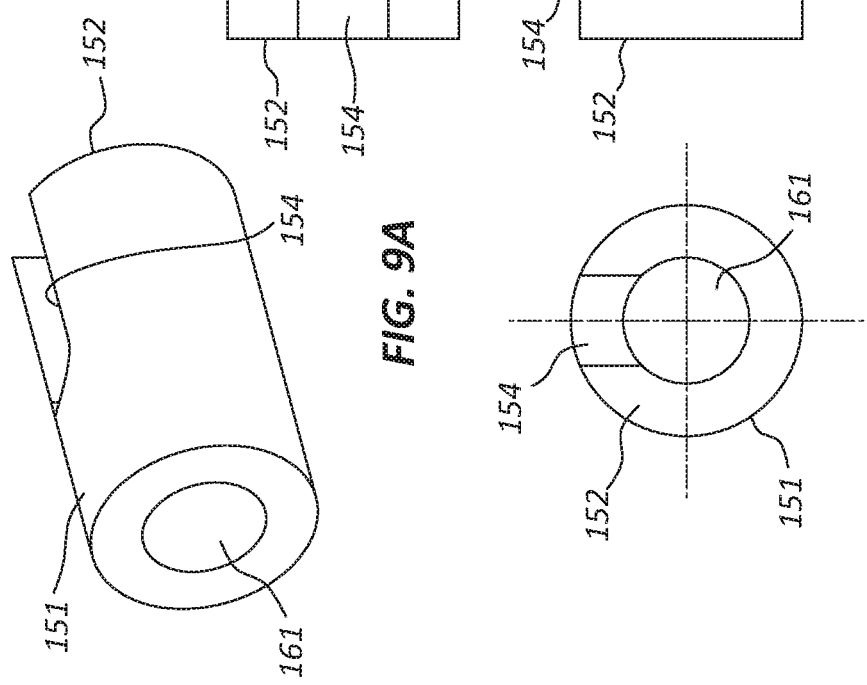
FIG. 9E
FIG. 9F

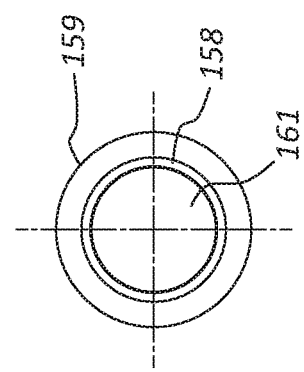
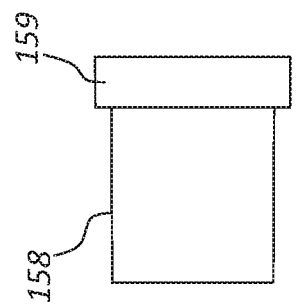
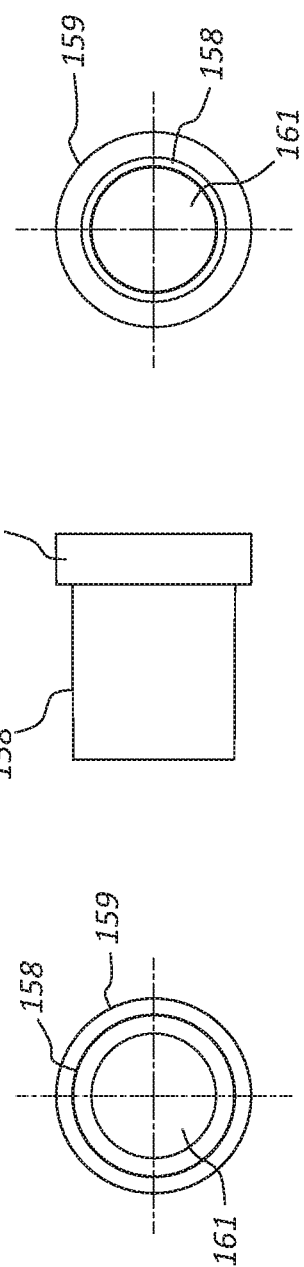
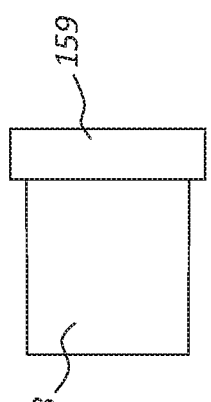
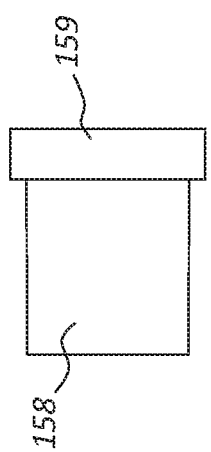
FIG. 10A
FIG. 10B
FIG. 10C
FIG. 10D
FIG. 10E
FIG. 10F

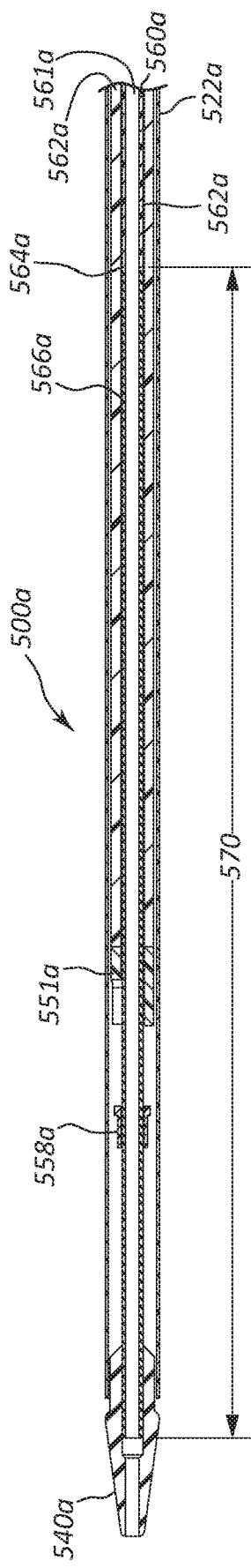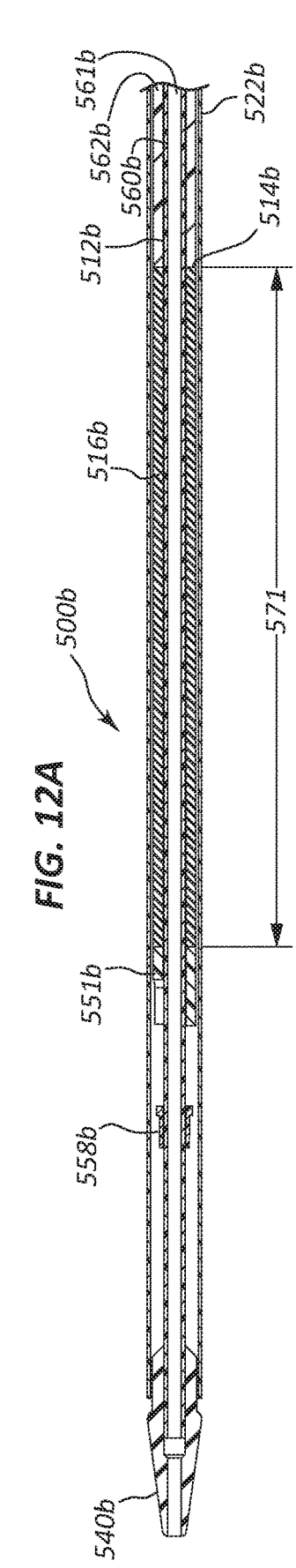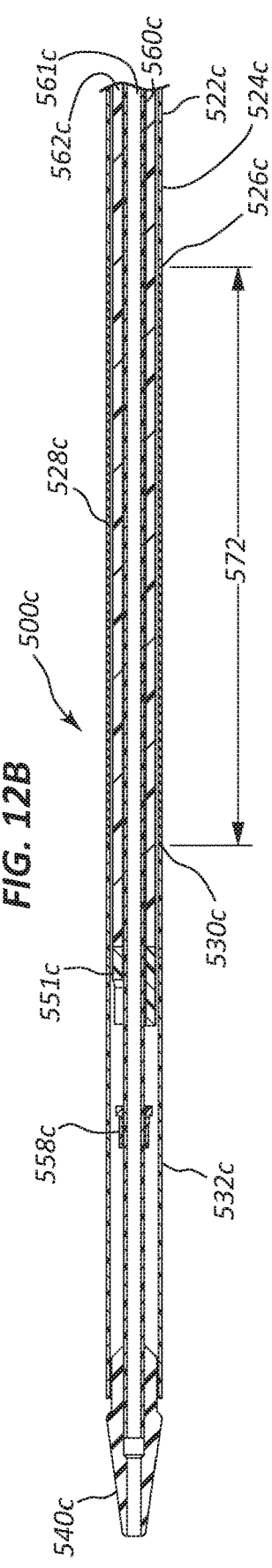

IMPLANTABLE DEVICE DELIVERY SYSTEM

RELATED APPLICATIONS

This application is a continuation of U.S. patent application Ser. No. 15/263,741, filed on Sep. 13, 2016 and titled "Implantable Device Delivery System," which claims priority to U.S. Provisional Application No. 62/218,892, filed on Sep. 15, 2015 and titled, "Implantable Device Delivery System," each of which is hereby incorporated by reference in its entirety.

TECHNICAL FIELD

The present disclosure relates generally to systems for delivering a crimped implantable device, such as an airway stent, into a lumen and deploying the implantable device at a site within the lumen.

BRIEF DESCRIPTION OF THE DRAWINGS

FIG. 1A is a perspective view of a delivery device according to one embodiment of the present disclosure in a delivery configuration.

FIG. 1B is an enlarged perspective view of the distal end of the delivery device shown in FIG. 1A in the delivery configuration with a section of an outer tubular member cut away.

FIG. 3A is a perspective view of the delivery device of FIG. 1A in a deployed configuration.

FIG. 3B is an enlarged perspective view of the distal end of the delivery device of FIG. 3A.

FIG. 6A is a cross-sectional view of a distal section of the delivery device of FIG. 5A.

FIG. 6B is an enlarged cross-sectional view of the distal end of the delivery device of FIG. 5A.

FIG. 7A is a perspective view of an embodiment of a tip to be used in a delivery device, shown from a distal vantage point.

FIG. 7B is a perspective view of the tip of FIG. 7A shown from a proximal vantage point.

FIG. 7C is a side view of the tip of FIG. 7A.

FIG. 7D is an end view of the proximal end of the tip of FIG. 7A.

FIG. 7E is an end view of the distal end of the tip of FIG. 7A.

FIG. 8A is a perspective view of another embodiment of a tip to be used in a delivery device, shown from a distal vantage point.

FIG. 8B is a perspective view of the tip of FIG. 8A shown from a proximal vantage point.

FIG. 8C is a side view of the tip of FIG. 8A.

FIG. 8D is an end view of the distal end of the tip of FIG. 8A.

FIG. 8E is an end view of the proximal end of the tip of FIG. 8A.

FIG. 9A is a perspective view of an embodiment of a pusher to be used in a delivery device, shown from a proximal vantage point.

FIG. 9B is a perspective view of the pusher of FIG. 9A shown from a distal vantage point.

FIG. 9C is a side view of the pusher of FIG. 9A.

FIG. 9D is a top view of the pusher of FIG. 9A.

FIG. 9E is a bottom view of the pusher of FIG. 9A.

FIG. 9F is an end view of the distal end of the pusher of FIG. 9A.

FIG. 9G is an end view of the proximal end of the pusher of FIG. 9A.

FIG. 10A is a perspective view of an embodiment of an anchor to be used in a delivery device, shown from a distal vantage point.

FIG. 10B is a perspective view of the anchor of FIG. 10A shown from a proximal vantage point.

FIG. 10C is a side view of the anchor of FIG. 10A.

FIG. 10D is a top view of the anchor of FIG. 10A.

FIG. 10E is an end view of the distal end of the anchor of FIG. 10A.

FIG. 10F is an end view of the proximal end of the anchor of FIG. 10A.

FIG. 12A is a cross-sectional view of another embodiment of a delivery device.

FIG. 12B is a cross-sectional view of another embodiment of a delivery device.

FIG. 12C is a cross-sectional view of another embodiment of a delivery device.

DETAILED DESCRIPTION

Figure 2A:
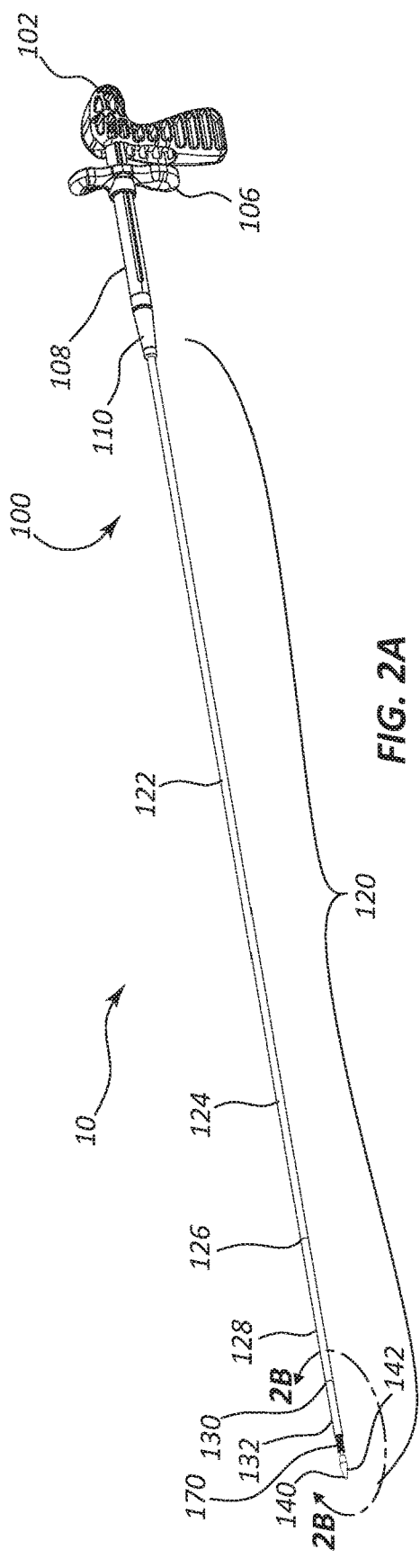
FIG. 2A is a perspective view of the delivery device of FIG. 1A in a partially deployed configuration during deployment.

Crimpable implantable devices can serve many purposes in the medical field. For example, stents are inserted into body lumens such as vessels or passages to keep the lumen open and prevent closure due to a stricture, external compression, or internal obstruction. In particular, some stents are designed to relieve difficult or labored breathing caused by a variety of health conditions, including but not limited to extrinsic or intrinsic compression, disease, and loss of cartilaginous support. Airway stenting, also known as tracheo-bronchial stenting, can relieve airway obstruction caused by strictures, disease, injury, etc. that may not be suitably treated by debridement, resection, reconstruction etc. Airway stenting can also provide structural support for an airway that has been damaged during a medical procedure.

Though many of the examples provided herein refer to stents configured for use within the airway (e.g., trachea, bronchus, bronchiole), the present disclosure is also applicable to a variety of stents and other crimpable implantable devices designed for a variety of applications in various lumens of the body such as the vasculature and the esophagus.

It will be readily understood with the aid of the present disclosure that the components of the embodiments, as generally described and illustrated in the figures herein, could be arranged and designed in a variety of configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the implantable devices disclosed herein. As used herein, the proximal end of a medical device is the end nearest a practitioner during use, while the distal end is the opposite end. For example, the proximal end of a stent refers to the end nearest the practitioner when the stent is disposed within, or being deployed from, a deployment apparatus. For consistency throughout, these terms remain constant in the case of a deployed stent, regardless of the orientation of the stent within the body. In the case of an airway stent—deployed through the mouth of a patient—the proximal end will be nearer the head of the patient and the distal end nearer the abdomen (or deeper into the lungs) when the stent is in a deployed position.

FIG. 1A depicts a delivery system 10 in a delivery configuration. The delivery system 10 is configured to deliver and deploy a crimped implantable device, such as an airway stent, into a lumen within a body. The delivery system 10 includes a delivery device 100 that may include one or more of a handle 102, a safety 104, a trigger 106, an outer support 108, a strain relief 110, a tubular member 120 and a tip 140. The delivery device has a longitudinal axis extending parallel to, and positioned radially centered in, the tubular member 120.

The handle 102 is configured to be easily grasped by a practitioner to secure and control the delivery device 100. In the illustrated embodiment of FIG. 1A, the handle 102 is shaped like the handle or butt of a handgun and configured to position the trigger 106 similar to the position of a trigger of a handgun. The handle 102 may be ergonomically configured to be comfortably gripped in a practitioner's hand.

The safety 104 can be constructed using any number of designs to prevent the unintentional deployment of the crimped implantable device by inhibiting retraction of the trigger 106. In the embodiment of FIG. 1A, the safety 104 is a removable spacer that prevents the trigger 106 from being retracted relative to the handle 102.

The trigger 106 is configured to be retracted (e.g., pulled) toward the handle 102 to retract an outer tubular member of the tubular member 120 and provide release (or deployment) of an implantable device. The trigger 106 may be supported by the outer support 108.

The outer support 108 may be rigid housing to enable retraction of the trigger 106 and to stabilize the delivery device 100 and prevent bending and kinking at the proximal end of the delivery device 100.

The strain relief 110 can be used to facilitate smooth deployment during a deployment process as discussed below.

The tubular member 120 extends distally from the strain relief 110 and/or outer support 108. The tubular member 120 may be formed of polymeric components, metal, or other suitable materials. The tubular member 120 may include an outer tubular member 122, one or more inward or more interior tubular members, and the tip 140. The outer tubular member 122 may be constructed or formed in a manner to provide variable rigidity along its length. This can be achieved a number of ways, including by creating multiple zones of distinct rigidity, alternating zones of at least two differing levels of rigidity, and creating differing levels of rigidity at differing layers of the tubular member 120. The outer tubular member 122 may include a first outer tubular member section 124 that extends distally from the proximal end of the delivery device 100. The first outer tubular member section 124 may be constructed to provide for a first desired rigidity. The desired rigidity may be provided by the material by which the first outer tubular member section 124 is formed. Alternatively, a stiffening coating may be applied to the surface of the first outer tubular member section 124 to achieve a first desired rigidity. A longitudinal wire inside, within, or outside of the first outer tubular member section 124 may also be used to achieve a desired rigidity.

The first outer tubular member section 124 may terminate at a first outer tubular member transition zone 126. The first outer tubular member section 124 may be heat molded, thermally laminated, or connected via re-flow to another section of the tubular member 120, thereby forming a first outer tubular member transition zone 126 between the first outer tubular member section 124 and a second outer tubular member section 128. The first outer tubular member transition zone 126 may be formed of a material having its own rigidity that extends a length along the tubular member 120. Furthermore, the first outer tubular member transition zone 126 may include an overlap of the materials of the first outer tubular member section 124 and the second outer tubular member section 128. Alternatively, the transition zone may be substantially two dimensional. A substantially two dimensional transition zone may be formed by using an adhesive between two abutting sections of the outer tubular member 120. It should be understood that all additional transition zones described herein may be similarly formed.

The outer tubular member 122 may further comprise the second tubular member section 128, which extends distally from the first outer tubular member transition zone 126. In some embodiments, the second tubular member section 128 has a second level of rigidity that can be achieved using any of the techniques described above. In some embodiments, the second outer tubular member section 128 abuts the tip 140. Alternatively, the second outer tubular member section 128 extends distally to a second outer tubular member transition zone 130 formed in any of the ways described above for forming the first outer tubular member transition zone 126. In some embodiments, a third outer tubular member section 132 with a third level of rigidity may extend distally from the second outer tubular member transition zone 130 to the tip 140. The most distal section of the outer tubular member may be referred to as a pod section of the outer tubular member 122 which houses a crimped implantable device 120 such as a stent.

In still further alternative embodiments, the outer tubular member 122 may include several outer tubular member sections and outer tubular member transition zones. The construction of the outer tubular member 122 in this manner provides several benefits. One such benefit of a delivery device 100 with variable rigidity is the ability to conform the delivery device 100 to a specific application of a crimpable implantable device. For example, it may be desirable to have a distal end of the tubular member 120 be less rigid than a proximal end, thereby allowing the distal end of the delivery device 100 to maneuver through a lumen (e.g., a highly tortuous lumen) of a patient with minimal damage to the walls of the lumen, while at the same time maintaining sufficient rigidity in a proximal section of the tubular member 120 to enable advancing the tip 140 of the delivery device 100 to a desired deployment location in the lumen of the patient.

The tip 140 is configured to be positioned at the distal end of the tubular member 120, and more particularly the most distal section 132 (or pod) of the outer tubular member 122, when the delivery device 100 is in a delivery configuration. The tip 132 may be formed of a molded plastic.

Also shown in FIG. 1 is a distal section 142 of the tip 140 that can be seen extending distally from the distal end of the outer tubular member 122. The distal section 142 of the tip 140 may be cone-shaped for ease of insertion into a lumen of a patient and to prevent damage to the lumen.

FIG. 1B is a close up perspective view of the distal end of the tubular member 120 of the delivery device 100 of FIG. 1A. with the outer tubular member 122 cut away to show a tip 140, a crimped implantable device 170, and components of a distal end of an inner assembly 150 of the tubular member 120 including a pusher 151 and an inner shaft member 160.

The crimped implantable device 170 of FIG. 1B may be a tracheobronchial stent 170 (or airway stent 170) formed by a plurality of struts 172 for providing structural support. One application of an airway stent 170 is for the treatment of tracheobronchial strictures and airway compression (stenosis) produced by malignant neoplasms. In some applications, the airway stent 170 is removable, making the airway stent suitable for treating benign conditions such as tracheoesophageal fistulae and strictures resulting from surgical anastomosis of a lumen in a body. The delivery system 10 is particularly useful for delivering small stents including airways stents that are 6×15 mm, 8×10 mm, 8×15 mm, 8×20 mm, 10×15 mm, 12×15 mm, and 14×15 mm. The features of the delivery system 10 enable the reduction of the profile of the delivery device 100 when in delivery configuration. An airway stent is constructed to have a crimped configuration for positioning of the airway stent in a delivery device, and an expanded configuration (e.g., a deployed configuration) for providing radial support to a lumen in a body. Example embodiments of the interstice geometry of a stent and methods of manufacturing the stent are disclosed in, for example, U.S. Patent Publication No. 20040127973, entitled "Removable Biliary Stent," and U.S. Patent Publication No. 20120310363, entitled "Esophageal Stent," each of which is hereby incorporated herein by reference.

The implantable device 170 may include a suture 155 coupled to its proximal end to facilitate removal or proximal movement of the implantable device 170 after deployment. The ends of the suture 155 are generally connected in a knot, clasp, crimp, or other similar binding method. When connecting the ends of the suture 155 using any of these binding methods, the connection may be further secured with an adhesive. FIG. 1B illustrates the suture 155 is bound with a clasp 156.

The added material of the suture clasp 156 or other binding mechanism or method can be significant relative to diameter of the crimped implantable device 170 such that in presently available delivery devices the suture clasp 156 would extend beyond a diameter of the crimped implantable device 170 and thus necessitate a larger or wider profile of the delivery device 100. More particularly, in a crimped state, the implantable device 170 may closely conform to an inner tubular member (e.g., such as may be part of an inner assembly such as inner assembly 150) to be received within the pod or distal section 132 of the outer tubular member 122. The clasp 156 may have a thickness that is greater than a wall of the crimped implantable device 170. When brought into close abutment with the inner tubular member of a presently available delivery device, the clasp 156 may protrude radially outward from the inner tubular member to a greater degree than an outer diameter of the crimped implantable device 170. Stated otherwise, the clasp 156 may extend radially outward beyond the crimped implantable device 170, such that the tubular member 120 may necessarily be larger to accommodate the clasp 156. A larger tubular member 120 can make inserting the tubular member 120 and deploying the implantable device 170 into a small lumen in the body more difficult. The present inventors recognize a desirability to reduce a diameter of the outer tubular member 122 for deploying a small implantable device into a small lumen. Certain embodiments of the present disclosure can include an accommodation for the clasp 156 and/or other binding mechanism to limit a diameter of the tubular member 120, as will be described below.

The pusher 151 includes a push surface 152 abutting the crimped implantable device 170 to restrict proximal movement of the crimped implantable device 170 relative to the inner assembly 150, particularly during deployment. As noted above, the implantable device 170 may include a suture to facilitate removal or movement of the implantable device 170 after deployment. The ends of the suture are connected in a clasp 156 or other binding mechanism that may have a profile. To reduce the profile of the delivery device 100, the pusher may be formed or constructed with a slot 154 to create a void in which the suture clasp 156 may be inserted and stored while the delivery device 100 is in a delivery configuration. Stated otherwise, the slot 154 can receive and accommodate the suture clasp 156 to limit an extent to which the clasp 156 extends beyond a circumference or diameter of the crimped implantable device 170.

Additionally, the pusher 151 may be formed out of, or impregnated with, radiopaque material to allow a practitioner to view the location of the pusher 151 using radio imaging. Because the pusher 151 abuts the proximal end of the crimped implantable device 170, the practitioner is able to use the position of the pusher 151 to more accurately place the crimped implantable device 170 within a lumen of a body.

The inner assembly 150 may further comprise an inner shaft member 160 connected to the tip 140. The inner shaft member 160 may extend proximally from the tip 140 to the proximal end of the tubular member 120 and define a lumen 161 to facilitate advancing the delivery device 100 along a guidewire for accurate positioning into a body lumen. In some embodiments of a delivery device, the lumen 161 extends from the distal end of the tip 140 to the proximal end of the handle 102. Additionally, the inner shaft member 160 may provide structural support for the implantable device 170, the tip 140, and one or more of the components at the distal end of the inner assembly 150 such as the pusher 151. The inner shaft member 160 may be formed of polymeric or other suitable material.

The tip 140, as shown, has a blunted distal end 141 to avoid having a sharp point at the distal end of the delivery device 100. In some embodiments, the distal section 142 of the tip 140 is rounded. The lumen 161 described above also passes through the tip. In some embodiments, the tip 140 further comprises a tip transition zone 144 that transitions the tip 140 from a circumference of the distal section 142 of the tip 140 to a proximal section 146 of the tip 140. This tip transition zone 144 may be a rounded circumferential surface, a chamfered edge, or other shaped edge formed to create a continuous transition to the proximal section of the tip 146. The tip transition zone 144 helps reduce catching or snagging of the tip 140 on the implantable device 170 or the anatomy of the body lumen during withdrawal of the tubular member 120 after deployment of the implantable device 170. The tip 140 may further include a second tip transition zone 148 that connects the tip 140 to the inner shaft member 160 via adhesive, friction fit, a locking mechanism, or other suitable connection means. Alternatively, the tip 140 and inner shaft member 160 may be formed as one integrated piece. Like the tip transition zone 144, the second tip transition zone 148 is designed to reduced catching or snagging of the tip 140 on the implantable device 170 or the anatomy of the body lumen during withdrawal of the tubular member 120 after deployment of the implantable device 170.

Figure 2B:
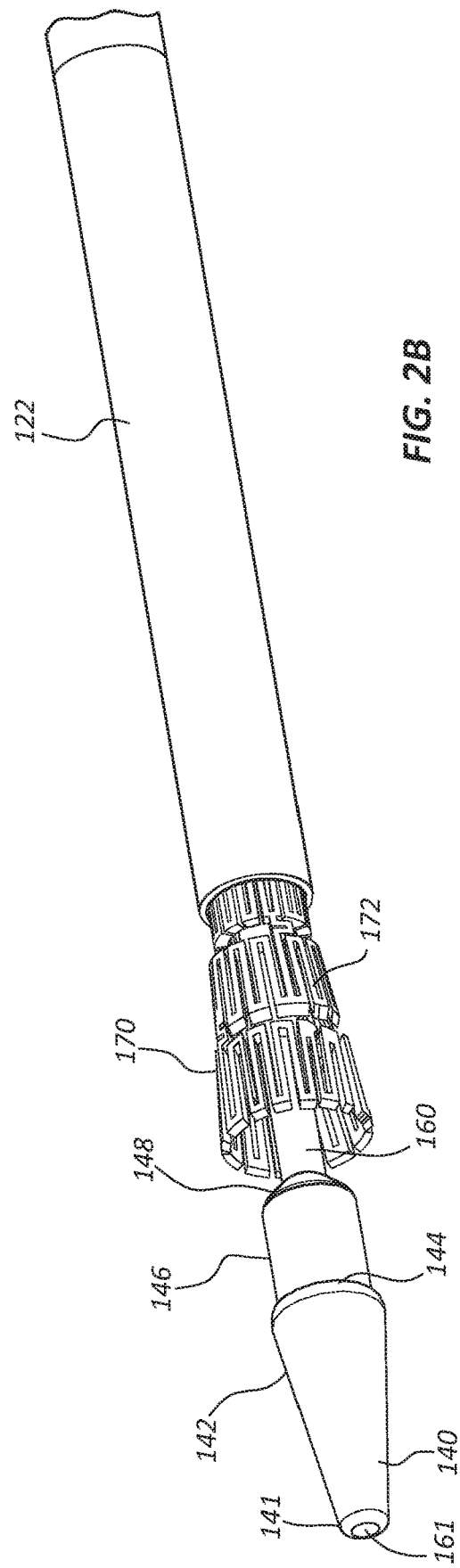
FIG. 2B is an enlarged perspective view of the distal end of the delivery device of FIG. 2A.

FIG. 2A is a perspective view of the delivery system 10 of FIG. 1A with the delivery device 100 in a partially deployed configuration during deployment of the implantable device 170. FIG. 2B is an enlarged perspective view of the distal end of the delivery device 100 in the partially deployed configuration of FIG. 2A. Referring to FIGS. 2A and 2B generally and collectively, the delivery device 100 is transitioning from the delivery configuration to a deployed configuration. The delivery device 100 shown includes the handle 102, the trigger 106, the outer support 108, and the strain relief 110 at the proximal end of the delivery device 100. In FIG. 2A, the delivery device 100 is lacking the safety 104 because it has been removed prior to retracting the trigger 106.

The configuration of the deployment device 100 may change from the delivery configuration as depicted in FIGS. 1A and 1B to a partially deployed configuration upon the retraction of the trigger 106 relative to the handle 102 as shown in FIGS. 2A-2B. Retraction of the trigger 106 toward the handle 102 may cause retraction of the outer tubular member 122 relative to the tip 140 and crimped implantable device 170. The outer tubular member 122 is coupled to trigger 106 such that manipulation of the trigger 106 by a practitioner operates the tubular member 120, to cause the outer tubular member 122 to move proximally relative to the inner assembly 150 (shown in FIG. 1B) to deploy the implantable device 170. When the outer tubular member 122 is no longer surrounding a portion of the crimped implantable device 170, that portion of the implantable device 170 is relieved of compressive force and expands to a deployed diameter. The diameter of the fully deployed implantable device 170 is greater than a largest diameter of the tip 140.

FIG. 3A is a perspective view of the delivery system 10 of FIG. 1A with the delivery device 100 in a deployed configuration. FIG. 3B is an enlarged perspective view of the distal end of the delivery device 100 in the deployed configuration of FIG. 3A. Referring to FIGS. 3A and 3B generally and collectively, the delivery device 100 is in a fully deployed configuration wherein the outer tubular member 122 has been retracted sufficiently so that the distal end of the outer tubular member 122 is proximal to the proximal end of the implantable device 170, thereby fully releasing the crimped implantable device 170 from the compressive force and permitting the entire implantable device 170 to expand to a deployed configuration.

When the implantable device 170 has expanded to a deployed configuration as shown in FIGS. 3A and 3B, the inner diameter of the implantable device 170 is greater than the greatest diameter of the tip 140, thereby enabling the tip 140 to be withdrawn through the lumen of the implantable device 170. During the withdrawal of the tip 140, the tip transition zone 144 and the second tip transition zone 148 may help prevent the tip from getting caught in the implantable device 170 or the suture clasp 156 or other binding method.

Referring to FIG. 3B specifically, an enlarged prospective view of the clasp 156 is shown outside of the slot 154 after the implantable device 170 is in a deployed configuration. Although the clasp 156 is shown completely ejected from the slot 154, in some embodiments, the clasp 156 or other binding method may continue to loosely rest within the slot 154 until the delivery device 100 is retracted from the lumen in the body.

Figure 4A:
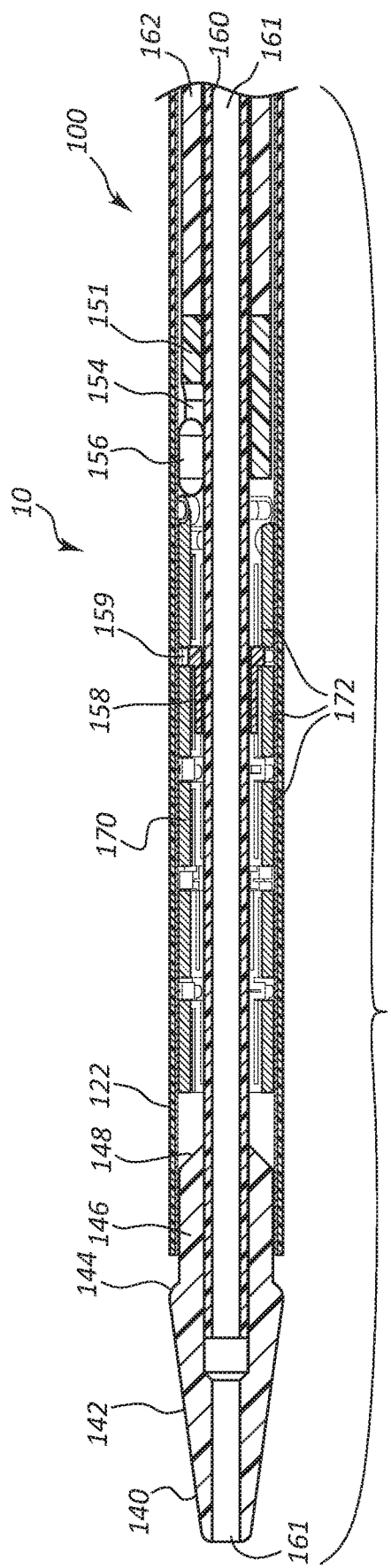
FIG. 4A is a cross-sectional view of the delivery device of FIG. 1A in the delivery configuration.
Figure 4B:
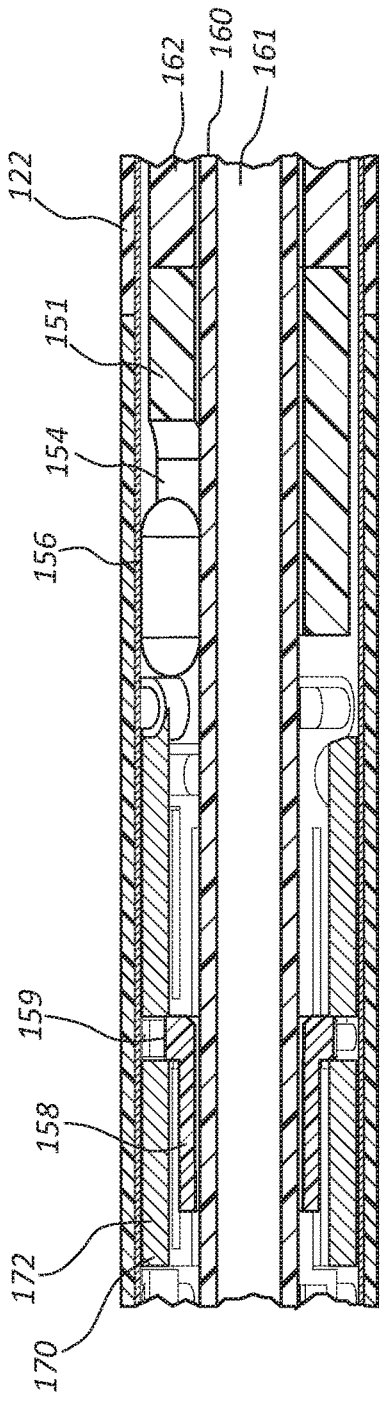
FIG. 4B is a cross-sectional view of the distal end of the delivery device of FIG. 4A.

FIG. 4A is a cross-sectional view of the delivery system 10 of FIG. 1A with the delivery device 100 in a delivery configuration. FIG. 4B is an enlarged cross-sectional view of a section of the delivery device 100 containing the clasp 156 in the delivery configuration of FIG. 4A. Referring to FIGS. 4A and 4B generally and collectively, the delivery device 100 is in a delivery configuration. In FIGS. 4A and 4B, the tubular member 120 of the delivery device 100 comprises at least three layers of tubular members disposed proximal to the pusher 151. The inner most component of the tubular member 120 may be an inner shaft member 160, which defines a lumen 420. The outer most tubular member comprises the outer tubular member 122. The middle tubular member comprises a mid-sheath 162. The inner shaft member 160 and the mid-sheath 162 may be referred to herein individually, or collectively, as an inner sheath. It should be understood that other embodiments may have only two of the three shown tubular members, or other differing combination of layers. Additionally, a lumen is not a necessary component of other embodiments. Furthermore, in some embodiments, the inner shaft member 160, the mid-sheath 162, or both may be components of the inner assembly 150. Stated differently, the inner assembly 150 may include an inner sheath.

FIGS. 4A and 4B also show the pusher 151 with the slot 154 and a suture clasp 156 disposed within the slot 154. Also shown is an anchor 158 with a flange 159 positioned within a proximal portion of a lumen of the crimped implantable device 170 to engage an inner surface or an inner wall of the crimped implantable device 170 (i.e., in a crimped state). As depicted in FIGS. 4A and 4B, the flange 159 fits securely between two rows of struts 172, forming a scaffolding structure of the crimped implantable device 170, to prevent proximal and distal movement of the crimped implantable device 170 relative to the anchor 158. In some embodiments, the flange 159 fits securely between the proximal most row of struts and the adjacent row of struts. The anchor 158 may be fixed at a location of the inner shaft member 160, the mid-sheath 162, or another component of the tubular member 120. In some embodiments, the anchor 158 may secure in place a proximal portion of a partially deployed stent or facilitate retraction of a partially deployed stent into a delivery configuration by being proximally moveable. Additionally, as will be described more fully below, the anchor 158 may be independent of the pusher 151, the anchor 158 may be connected to the pusher 151, or the anchor 158 and pusher 151 may be one individually formed component.

FIGS. 4A and 4B also show an approximate size of the clasp 156 relative to the struts 172 of the implantable device 170. In many embodiments, the clasp 156 has a larger radial profile than that of the struts 172. As seen specifically in FIG. 4B, the void formed by the slot 154 to house the clasp 156 allows the placement of the clasp 156 more radially inward than if the clasp 156 was radially outside of the pusher 151. Thus, the profile of the tubular member 120 is reduced using the technology disclosed in this embodiment.

Figure 5A:
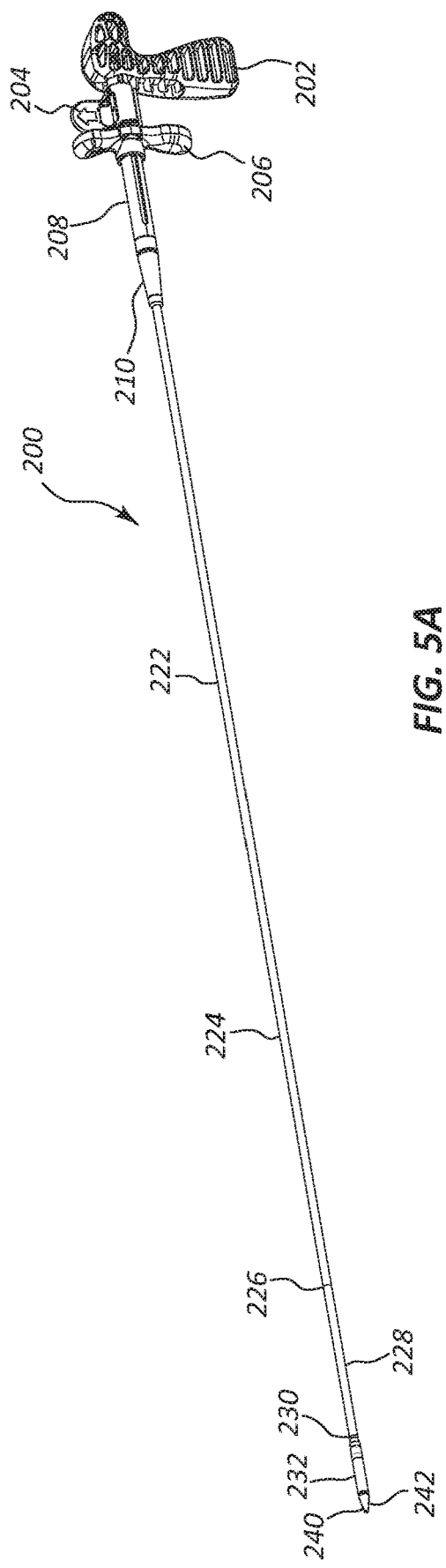
FIG. 5A is a perspective view of a delivery device according to another embodiment of the present disclosure in delivery configuration.
Figure 5B:
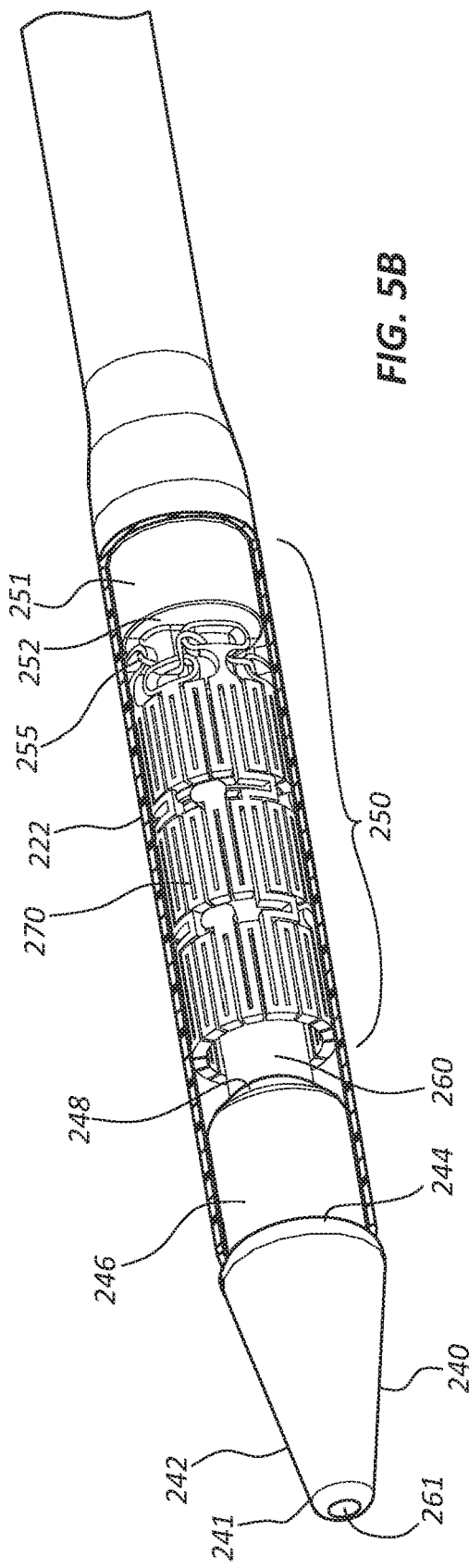
FIG. 5B is an enlarged perspective view of the distal end of the delivery device of FIG. 5A with a section of an outer tubular member cut away.

FIG. 5A is a perspective view of a new embodiment of a delivery device 200 in a delivery configuration wherein a distal section of an outer tubular member 222, depicted as a third outer tubular member section 232, has a diameter greater than that of a first outer tubular member section 224. FIG. 5B is an enlarged perspective view of the distal end of the delivery device 200 in the delivery configuration of FIG. 5A. Referring to FIGS. 5A and 5B generally and collectively, the delivery device 200 is in a delivery configuration. In some embodiments, the third outer tubular member section 232 may be referred to as a "pod" section of the outer tubular member 222. The pod section may house a pusher 251, an implantable device 270, a portion of an inner shaft member 260 and a proximal section 246 of a tip 240. Delivery device 200 may have additional analogous features to those of delivery device 100 depicted in FIGS. 1A-4B. These analogous features are labeled with a similar numbering system as those of FIGS. 1A-4B but with the first digit changed from the number 1 to the number 2. For example, tip 240 of FIG. 5A is analogous to tip 140 of FIG. 1A and outer tubular member 222 of FIG. 5A is analogous to outer tubular member 122 of FIG. 1A.

FIG. 6A is a cross-sectional view of the delivery system 200 of FIG. 5A with the delivery device 200 in a delivery configuration. FIG. 6B is an enlarged cross-sectional view of a section of the delivery device 200 containing the clasp 256 in the delivery configuration of FIG. 6A. Referring to FIGS. 6A and 6B generally and collectively, the delivery device 200 is in a delivery configuration. In the delivery device 200 of FIGS. 6A and 6B, a pusher 251 and an anchor 258 having a flange 259 are one solitary or integral component referred to as a panchor 253. In the optional configuration depicted, a suture clasp 256 of an implantable device 170 in a crimped state in the delivery configuration is housed between the anchor 258 and the pusher 251 in a void 254 (e.g., a slot) formed in the panchor 253 between a pusher surface 252 and the flange 259 of the anchor. In this configuration, the pusher 251 and the anchor 258 may be connected via one or more connecting pieces 253. The void 254 (or slot) may be defined in/by the one or more connecting pieces 253.

FIGS. 7A-7E show various views of the tip 140 of the delivery device 100 of FIG. 1A. FIG. 7A is a perspective view of an embodiment of a tip to be used in a delivery device, shown from a distal vantage point. FIG. 7B is a perspective view of the tip of FIG. 7A shown from a proximal vantage point. FIG. 7C is a side view of the tip of FIG. 7A. FIG. 7D is an end view of the proximal end of the tip of FIG. 7A. FIG. 7E is an end view of the distal end of the tip of FIG. 7A. Referring to FIGS. 7A-7E generally and collectively, The tip 140 includes a blunted distal end 141, a distal section 142, a tip transition zone 144, a proximal section 146, and a second tip transition zone 148. Also shown is a lumen 161 extending the length of the tip 140. As shown in the Figures, the tip transition zone 144 may be a rounded circumferential surface, a chamfered edge, or other shaped edge formed to create a continuous transition to the proximal section of the tip 146 and reduce the damage done to the interior of a body lumen upon insertion or withdrawal of the delivery device 200. The tip 140 may further include a second tip transition zone 148 that connects the tip 140 to the inner shaft member 160 via adhesive, friction fit, locking mechanism, over-mold, or other suitable connection means.

FIGS. 8A-8E show various views of an alternate tip 340 having a lumen 361, a blunted distal end 341, a distal section of the tip 342, a tip transition zone 344, a proximal portion 346 and a second tip transition zone 348. FIG. 8A is a perspective view of another embodiment of a tip to be used in a delivery device, shown from a distal vantage point. FIG. 8B is a perspective view of the tip of FIG. 8A shown from a proximal vantage point. FIG. 8C is a side view of the tip of FIG. 8A. FIG. 8D is an end view of the distal end of the tip of FIG. 8A. FIG. 8E is an end view of the proximal end of the tip of FIG. 8A. This embodiment of the tip 340 has an additional recess 349 on the proximal end of the tip. The recess 349 may be used to connect the tip 340 to an inner shaft member (not shown in these figures). Alternatively, the recess 349 may receive and abut a free-floating tube (e.g. spacer) that extends between the recess 349 and a panchor (not shown). This connection may be made via adhesive, friction fit, or locking mechanism. During the withdrawal of the tip 340, the tip transition zone 344 and the second tip transition zone 348 may help prevent the tip 340 from catching or snagging on an implantable device (not shown) or the anatomy of a body lumen during withdrawal of a deployment device (not shown) after deployment of the implantable device.

FIGS. 9A-9G provide various views of pusher 151 shown in FIGS. 1A-4B. FIG. 9A is a perspective view of an embodiment of a pusher to be used in a delivery device, shown from a proximal vantage point. FIG. 9B is a perspective view of the pusher of FIG. 9A shown from a distal vantage point. FIG. 9C is a side view of the pusher of FIG. 9A. FIG. 9D is a top view of the pusher of FIG. 9A. FIG. 9E is a bottom view of the pusher of FIG. 9A. FIG. 9F is an end view of the distal end of the pusher of FIG. 9A. FIG. 9G is an end view of the proximal end of the pusher of FIG. 9A. The pusher 151 includes a lumen 161, a push surface 152, and a slot 154 creating a void for receiving and accommodating a suture (not shown in these figures) or a suture binding mechanism (not shown in these figures). Additionally, the push surface 152 may be disposed orthogonal to the lumen 161 through the pusher 151, or the push surface 152 may be disposed obliquely to the lumen 161 through the pusher 151. The slot 154 is configured to house at least a portion of a clasp (not shown), thereby facilitating a more radially inward placement of the clasp and reducing the overall profile of a delivery device, while still maintaining the advantage of using a push surface 152 to restrict proximal movement of an implantable device (not shown) during deployment. The slot 154 may be a cutout of the pusher 151 that extends proximally from the distal end of the pusher 15. The cutout may extend from an outer surface of the pusher 151 to the lumen 161, or alternatively, extend radially inward to an inner surface (not shown in these figures). A proximal end of the slot 154 may be rounded for easier placement and removal of the suture binding mechanism FIGS. 10A-10F provide various views of an anchor 158 having a flange 159 and a lumen 161. FIG. 10A is a perspective view of an embodiment of an anchor to be used in a delivery device, shown from a distal vantage point. FIG. 10B is a perspective view of the anchor of FIG. 10A shown from a proximal vantage point. FIG. 10C is a side view of the anchor of FIG. 10A. FIG. 10D is a top view of the anchor of FIG. 10A. FIG. 10E is an end view of the distal end of the anchor of FIG. 10A. FIG. 10F is an end view of the proximal end of the anchor of FIG. 10A. In some embodiments, the anchor 158 is a component of an inner assembly of a delivery device. In some embodiments, the anchor 158 is mounted to an inner shaft member and the flange is configured to engage struts of an implantable device (not shown) and thereby restrict longitudinal displacement of the implantable device relative to the inner shaft member.

Figure 11B:
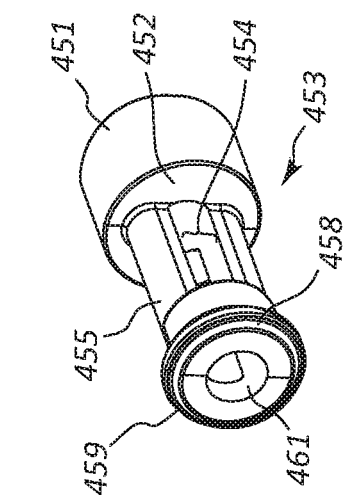
FIG. 11B is a perspective view of the panchor of FIG. 11A, shown from a proximal vantage point.
Figure 11G:
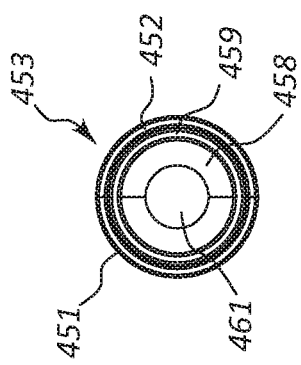
FIG. 11G is an end view of the distal end of the panchor of FIG. 11A.
Figure 11D:
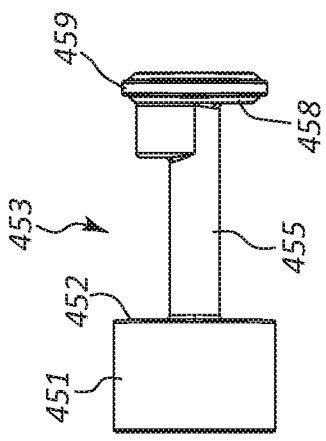
FIG. 11D is a top view of the panchor of FIG. 11A.
Figure 11C:
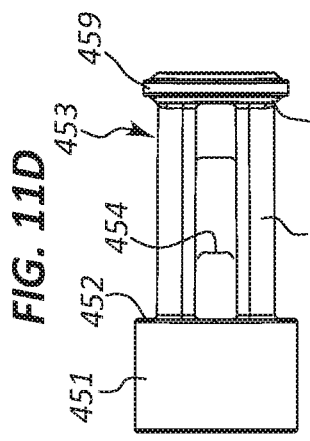
FIG. 11C is a side view of the panchor of FIG. 11A.
Figure 11E:
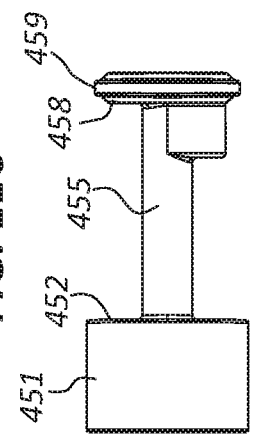
FIG. 11E is a bottom view of the panchor of FIG. 11A.
Figure 11A:
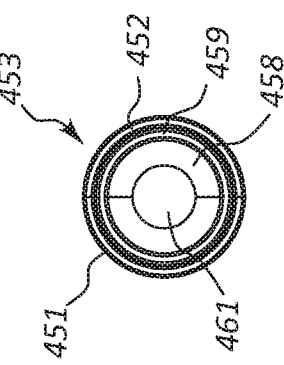
FIG. 11A is a perspective view of an embodiment of a panchor to be used in a delivery device, shown from a distal vantage point.
Figure 11F:
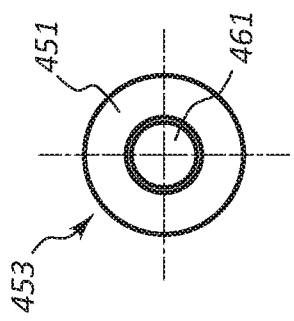
FIG. 11F is an end view of the proximal end of the panchor of FIG. 11A.

FIGS. 11A-11G provide various views of an alternate embodiment of a panchor 453 (of an inner assembly) that includes an anchor 458 and a pusher 451 as a single component connected by one or more connector pieces 455 spanning a distance between the push surface 452 and the anchor 458. FIG. 11A is a perspective view of an embodiment of a panchor to be used in a delivery device, shown from a distal vantage point. FIG. 11B is a perspective view of the panchor of FIG. 11A, shown from a proximal vantage point. FIG. 11C is a side view of the panchor of FIG. 11A. FIG. 11D is a top view of the panchor of FIG. 11A. FIG. 11E is a bottom view of the panchor of FIG. 11A. FIG. 11F is an end view of the proximal end of the panchor of FIG. 11A. FIG. 11G is an end view of the distal end of the panchor of FIG. 11A. The anchor 458 includes a flange 459 that may be analogous to the flange 159 of FIGS. 10A-10F and that is to be positioned within a proximal portion of a lumen of a crimpable implantable device to engage an inner wall of the implantable device in a crimped state. The pusher 451 includes a push surface 452 that is analogous to the push surface 152 of FIGS. 9A-9G. The panchor may also include a lumen 461 that extends the length of the panchor 453. In some configurations, the lumen 461 is configured to facilitate fitting the panchor 453 around an inner shaft member. Additionally, the anchor 458 may be positioned distal to the push surface 452 of the pusher 451 when the panchor 453 is installed in a delivery system.

FIG. 12A is a cross-sectional view of a distal section of a delivery device 500a, according to another embodiment. The delivery device 500a includes a tip 540a, a lumen 561a, an inner shaft member 560a, a mid-sheath 562a, an outer tubular member 522a, an anchor 558a, and a pusher 551a that are analogous to the tip 140, lumen 161, inner shaft member 160, mid-sheath 162, outer tubular member 122, anchor 158, and pusher 151 of FIGS. 1A-4B. The delivery device 500a of FIG. 12A has an inner shaft member 560a with variable rigidity along a length of the inner shaft member 560a. The inner shaft member 560a has a first inner shaft member section 563a with a first rigidity, a first inner shaft member transition zone 564a, and a second inner shaft member section 566a with a second rigidity. The first inner shaft member section 563a has a uniform rigidity that is distinct from the rigidity of the second inner shaft member section 566a. In other embodiments, the first inner shaft member section 563a has a rigidity greater than that of the second inner shaft member section 566a. In FIG. 12A, the second inner shaft member section 566a has a relatively low rigidity (or relatively high flexibility) that causes the inner shaft member 560a to have a zone 570 that is more flexible than at least one other section of the inner shaft member 560a, thereby affecting the rigidity along a length of the zone 570 of the deployment device 500a. In some embodiments the inner shaft member 560a includes additional sections and transition zones distal to the second inner shaft member section 566a. In some embodiments, a first inner shaft member section is distal to a first inner shaft member transition zone and a second inner shaft member section.

FIG. 12B is a cross-sectional view of a distal section of a delivery device 500b, according to another embodiment. The delivery device 500b includes a tip 540b, a lumen 561b, an inner shaft member 560b, a mid-sheath 562b, an outer tubular member 522b, an anchor 558b, and a pusher 551b that are analogous to the tip 140, lumen 161, the inner shaft member 160, the mid-sheath 162, the outer tubular member 122, the anchor 158, and the pusher 151 of FIGS. 1A-4B. The delivery device 500b has a mid-sheath 562b with variable rigidity along the length of the mid-sheath 562b. The mid-sheath 562b has a first mid-sheath section 512b with a first rigidity, a first mid-sheath transition zone 514b, and a second mid-sheath section 516b with a second rigidity. In some embodiments, the first mid-sheath section 562b has a uniform rigidity that is distinct from the rigidity of the second mid-sheath section 566b. In the illustrated delivery device 500b, the first mid-sheath section 562b has a relatively high rigidity and the second mid-sheath section 566b has a relatively low rigidity (or relatively high flexibility) that causes the mid-sheath to have a zone 571 that is more flexible than at least one other section of the mid-sheath 561b. In other embodiments, the rigidity of a second mid-sheath section 566b is greater than that of a third mid-sheath section (not shown in the figures). In still other embodiments, the mid-sheath 560b includes additional sections and transition zones distal to the second mid-sheath section 566b. In still other embodiments, a first mid-sheath section is distal to a first mid-sheath transition zone and a second mid-sheath section.

FIG. 12C is a cross-sectional view of a distal section of a delivery device 500c, according to another embodiment. The delivery device 500c includes a tip 540c, lumen 561c, inner shaft member 560c, mid-sheath 562c, outer tubular member 522c, anchor 558c, and pusher 551c that are analogous to the tip 140, lumen 161, inner shaft member 160, mid-sheath 162, outer tubular member 122, anchor 158, and pusher 151 of FIGS. 1A-4B. The delivery device 500c has an outer tubular member 522c with variable rigidity along the length of the outer tubular member 522c. The outer tubular member 522c has a first outer tubular member section 524b with a first rigidity, a first outer tubular member transition zone 526b, a second outer tubular member section 528c with a second rigidity, a second outer tubular member transition zone 530c, and a third outer tubular member section 532c with a third rigidity. The first outer tubular member section 554c of the delivery device 500c has a uniform rigidity that is distinct from the rigidity of at least one of the second outer tubular member section 566b and the third outer tubular member section 532c. In other embodiments, the first outer tubular member section 524c has rigidity greater than that of the second outer tubular member section 528c. Additionally, in other embodiments, the second outer tubular member section 528c has rigidity greater than that of the third outer tubular member section 532c. In some embodiments, the outer tubular member 522c includes additional sections and transition zones distal to the second outer tubular member section 524c. In the delivery device 500c of FIG. 12C, the second outer tubular member section 528c has a relatively low rigidity (or relatively high flexibility) that causes the outer tubular member 522c to have a zone 572 that is more flexible than at least one other section of the outer tubular member 522c, thereby affecting the rigidity along a length of the zone 572 of the deployment device 500c. In some embodiments the outer tubular member 522c includes additional sections and transition zones distal to the second outer tubular member section 528c. In some embodiments of the delivery device 500c, a first outer tubular member section is distal to a first outer tubular member transition zone and a second outer tubular member section.

Figure 13:
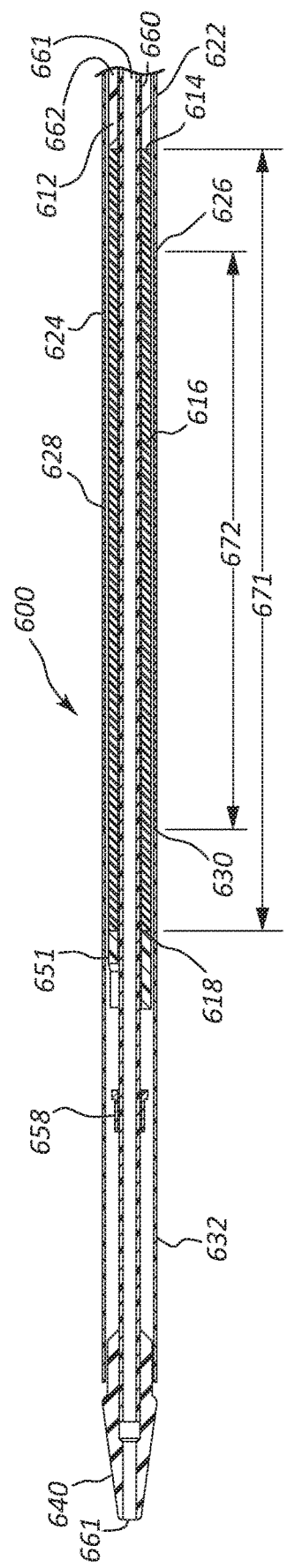
FIG. 13 is a cross-sectional view of another embodiment of a delivery device.

FIG. 13 is a cross-sectional view of a distal section of a delivery device 600, according to another embodiment. The delivery device 600 includes a tip 640, an outer tubular member 622 of variable rigidity, an inner assembly that includes an inner shaft member 660, a mid-sheath 662, a pusher 651, and an anchor 658. The mid-sheath 662 may have a first mid-sheath section 612, a first mid-sheath transition zone 614, and a second mid-sheath section 616. The second mid-sheath section has a rigidity distinct from the rigidity of the first mid-sheath section. In some embodiments, the first mid-sheath section has a uniform rigidity and the second mid-sheath section has a second uniform rigidity. In some embodiments, the section of the mid-sheath 622 with the least rigidity is positioned at the distal end of the mid-sheath 662. The transition zones can be formed or constructed using any of the techniques described herein.

The outer tubular member 622 may have a first outer tubular member section 624, a first outer tubular member transition zone 626, and a second outer tubular member section 628. The second outer tubular member section has a rigidity distinct from the rigidity of the first outer tubular member section. In some embodiments, the first outer tubular member section has a uniform rigidity and the second outer tubular member section has a second uniform rigidity. In some embodiments, the outer tubular member 622 has a second outer tubular member transition zone 630 distal to the second outer tubular member section 628 and a third outer tubular member section 630 distal to the second outer tubular member transition zone 632. In some embodiments, the third outer tubular member section 632 has a uniform rigidity that is distinct from the rigidity of the second outer tubular member section 628. In some embodiments, the section of the outer tubular member 622 with the least rigidity is positioned at the distal end of the outer tubular member 622. The transition zones can be formed or constructed using any of the methods described in the formation or construction described herein.

In some embodiments, the first outer tubular member transition zone 626 is longitudinally offset from the first mid-sheath transition zone 614. In some embodiments, the second outer tubular member transition zone 630 is offset from the second mid-sheath transition zone 618. Offsetting the first outer tubular member transition zone 626 from the first mid-sheath transition zone 614 gives the delivery device 600 sufficient stability at both the first outer tubular member transition zone 626 and the first mid-sheath transition zone 614 to prevent kinking while maintaining the desired flexibility along a length of the delivery device 600 needed to navigate various body lumens.

Figure 14A:
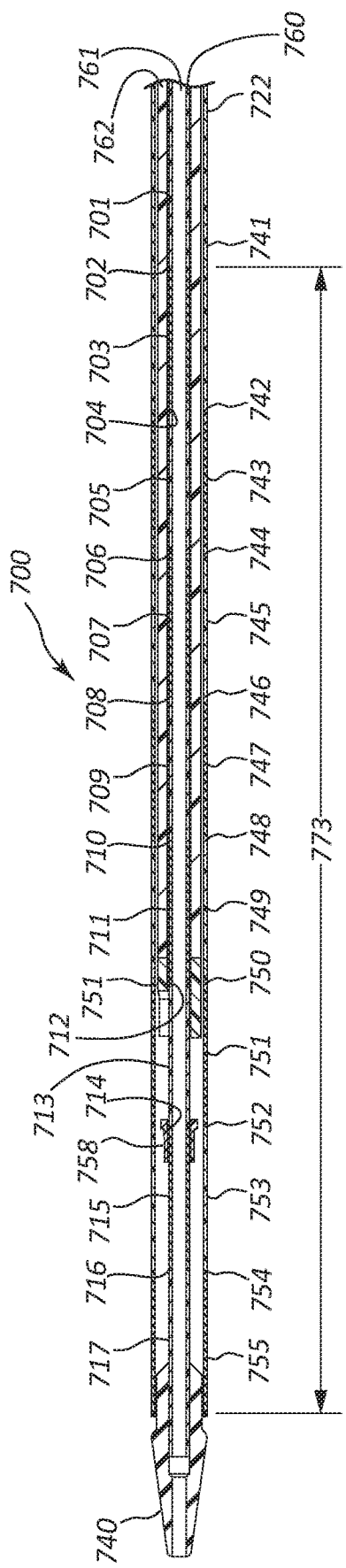
FIG. 14A is a cross-sectional view of another embodiment of a delivery device.

FIG. 14A is a cross-sectional view of a distal section of another embodiment of a delivery device 700. The delivery device 700 includes a tip 700, a lumen 761, an inner shaft member 760 a mid-sheath 762, an outer tubular member 722, an anchor 758, and a pusher 751 that are analogous to the tip 140, lumen 161, inner shaft member 160, mid-sheath 162, outer tubular member 122, anchor 158, and pusher 151 of FIGS. 1A-4B. The delivery device 700 has a flex zone 773 wherein an inner shaft member 760 and an outer tubular member 722 each have a plurality of sections of various rigidity. In another embodiment of a delivery device, the flex zone 773 is disposed proximal to the pusher 712. The inner shaft member 760 has inner shaft member sections 701, 703, 705, 707, 709, 711, 713, 715, 717 wherein each inner shaft member section has a rigidity that is distinct from the rigidity of the inner shaft member section immediately proximal to, and immediately distal to, the inner shaft member section. The inner shaft member 760 has inner shaft member transition zones 702, 704, 706, 708, 710, 712, 714, and 716 connecting adjacent inner shaft member sections using any of the transition zone forming or constructing methods disclosed herein. Similarly, the outer tubular member 722 has outer tubular member sections 741, 743, 745, 747, 749, 751, 753, 755 wherein each section has a rigidity that is distinct from the rigidity of the outer tubular member section immediately proximal to, and immediately distal to, the outer tubular member section. The outer tubular member 722 has outer tubular member transition zones 742, 744, 746, 748, 750, 752, and 754 connecting adjacent outer tubular member sections using any of the transition zone forming or construction methods disclosed herein. The various sections of the inner shaft member 760 and the various sections of the outer tubular member 722 can be combined to create a delivery device 700 that is specially configured to maneuver within the contours of a particular body lumen. For example, the delivery device 700 may be specifically designed with flexible sections at various positions on the delivery device 700 correlating to bends in the body lumen to reduce stress and injury to the body lumen.

Figure 14B:
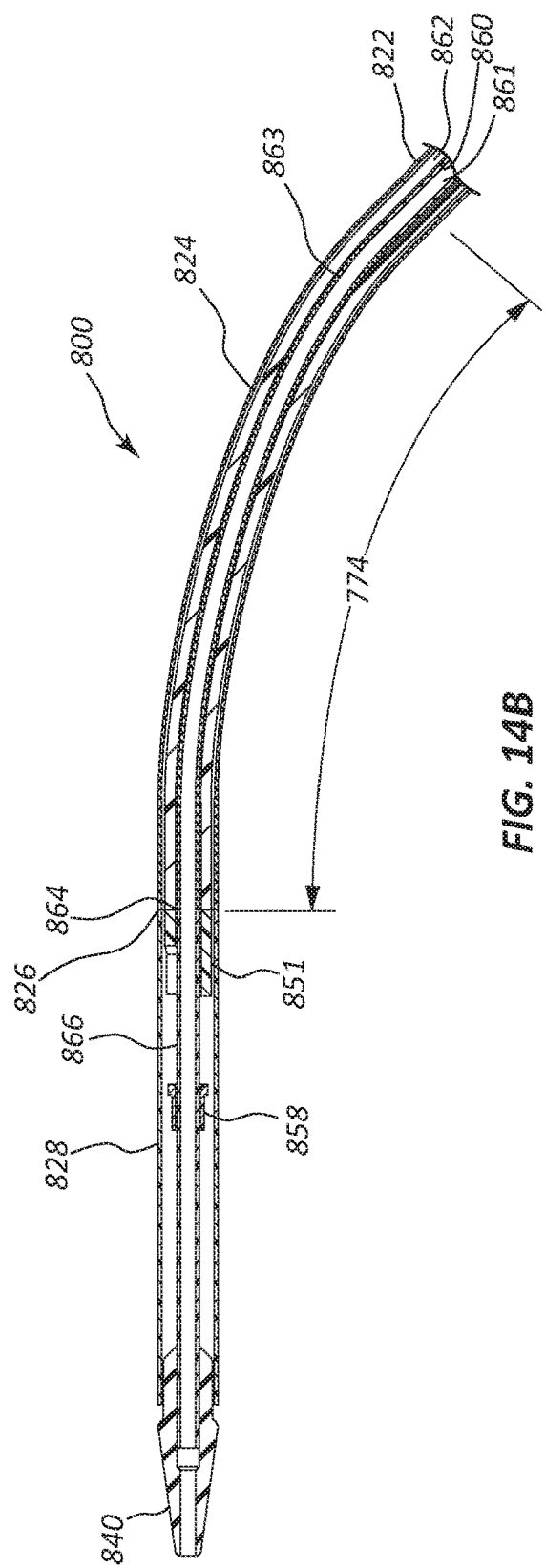
FIG. 14B is a cross-sectional view of the delivery device of FIG. 14A in a bent state.

FIG. 14B depicts another embodiment of a delivery device 800 that is shown bending through a flexible zone 874 that terminates distally at the pusher. In this embodiment, the inner shaft member 860 has a first inner shaft member section 863 and a first outer tubular member section 824 having less rigidity than a second inner shaft member section 866 and second outer tubular member section 828, thereby creating the flexible zone 774 of the delivery device 800 which may help to navigate a lumen of a body while causing minimal trauma to the interior of the lumen in the body.

In some embodiments, two or more of an inner shaft member, mid-sheath, and outer tubular member have variable rigidity along the length of the deployment device. Some of these embodiments have transition zones of two or more of an inner shaft member, a mid-sheath, and an outer tubular member that are longitudinally offset. This provides for a smoother transition between a more rigid section of a delivery device and a less rigid section of a delivery device and may reduce kinking or crimping at a transition zone.

Various embodiments as disclosed herein may incorporate one or more of the features described above. For example, one embodiment of the present disclosure is a delivery device having (1) an outer tubular member with variable rigidity having two sections of distinct rigidity that meet at a transition zone; (2) a tip with a lumen having a blunted distal end, a distal section, a tip transition zone creating a smooth transition from the distal section to a proximal section of the tip, and a second tip transition zone attaching the tip to an inner shaft member; and (3) an inner assembly with an inner shaft member, a mid-sheath with variable rigidity having at two sections of distinct rigidity that meet at a transition zone that is longitudinally offset from the outer tubular member transition zone, a pusher having a push surface to prevent proximal movement of a crimpable implantable device such as an airway stent and a slot to house ends of a suture, suture crimp, or suture clasp, an anchor positioned distal to the pusher having a flange to engage and prevent movement relative to the inner assembly of a crimpable implantable device during delivery configuration, and a crimpable implantable device housed within the outer tubular member and around the inner shaft member.

The examples and embodiments disclosed herein are to be construed as merely illustrative and exemplary, and not a limitation of the scope of the present disclosure in any way. It will be apparent to those having skill with the aid of the present disclosure in the art that changes may be made to the details of the above-described embodiments without departing from the underlying principles of the disclosure herein. It is intended that the scope of the invention be defined by the claims appended hereto and their equivalents.

The invention claimed is:

1. A delivery system for deploying an implantable device within a lumen of a body of a patient, the delivery system comprising:
    a delivery device to position an implantable device at a target location within a lumen of a body of a patient, the delivery device transitionable from a delivery configuration to a deployment configuration to deploy the implantable device at the target location, the delivery device including an outer tubular member that, in the delivery configuration, houses the implantable device in a crimped state for delivery to the target location and an inner assembly that is disposed within the outer tubular member, wherein at least one of the inner assembly and the outer tubular member is slidably movable relative to the other; and
    a pusher disposed at a distal portion of the inner assembly and within a distal portion of the outer tubular member and configured to engage a proximal portion of the implantable device in the crimped state within the outer tubular member in the delivery configuration, wherein the pusher comprises:
        a push surface facing distally to abut a proximal facing surface of the implantable device in the crimped state and limit proximal movement of the implantable device relative to the pusher during deployment as the delivery device transitions from the delivery configuration to the deployed configuration; and
        a slot to receive and house one or more of (i) ends of a suture coupled to the implantable device, (ii) a knot in the suture, and (iii) a clasp securing the ends of the suture, wherein the slot extends longitudinally in a proximal direction from the push surface of the pusher along a second surface of the pusher to form a void in the push surface and the second surface of the pusher.

2. The delivery system of claim 1, further comprising a tip disposed at a distal end of the inner assembly, the tip comprising a distal section, a proximal section, and a tip transition zone,
    wherein a diameter of a proximal most end of the distal section is greater than a diameter of a distal most end of the proximal section, and
    wherein the tip transition zone is a chamfered step to create a smooth transition between the proximal most end of the distal section and the distal most end of the proximal section.

3. The delivery system of claim 1, wherein the inner assembly further comprises an inner sheath positioned inside of the outer tubular member and extending proximally from the pusher, and
    wherein the inner sheath comprises a first inner sheath section extending distally from a proximal end to a first inner sheath transition zone and a second inner sheath section extending distally from the first inner sheath transition zone, the first inner sheath section having a first rigidity and the second inner sheath section having a second rigidity that is distinct from the first rigidity.

4. The delivery system of claim 3, wherein the outer tubular member comprises a first outer tubular member section extending distally from a proximal end to a first outer tubular member transition zone and a second outer tubular member section extending distally from the first outer tubular member transition zone, the first outer tubular member section having a third rigidity and the second outer tubular member section having a fourth rigidity that is distinct from the third rigidity.

5. The delivery system of claim 4, wherein the first inner sheath transition zone is offset along the length of the delivery system from the first outer tubular member transition zone.

6. A delivery system for deploying an implantable device within a lumen of a body of a patient, the delivery system comprising:
    a delivery device to position an implantable device at a target location within a lumen of a body of a patient, the delivery device transitionable from a delivery configuration to a deployment configuration to deploy the implantable device at the target location, the delivery device including an outer tubular member that, in the delivery configuration, houses the implantable device in a crimped state for delivery to the target location and an inner assembly that is disposed within the outer tubular member, wherein at least one of the inner assembly and the outer tubular member is slidably movable relative to the other; and
    a panchor disposed at a distal portion of the inner assembly and within a distal portion of the outer tubular member, wherein the panchor comprise an anchor and a pusher, the anchor configured to engage the implantable device in the crimped state at a position distal to a proximal end of the implantable device and to limit distal movement of the implantable device during deployment as the delivery device transitions from the delivery configuration to the deployed configuration.

7. The delivery system of claim 6, wherein the anchor of the panchor comprises a flange at a distal end of the panchor, the flange configured to be positioned within a proximal portion of a lumen of the implantable device and to engage an inner wall of the implantable device in the crimped state.

8. The delivery system of claim 6, wherein the panchor comprises a slot to receive and house one or more of (i) ends of a suture coupled to the implantable device, (ii) a knot in the suture, and (iii) a clasp securing the ends of the suture.

9. The delivery system of claim 6, wherein the pusher comprises a push surface facing distally to abut a proximal facing surface of the implantable device in the crimped state and limit proximal movement of the implantable device relative to the pusher during deployment as the delivery device transitions from the delivery configuration to the deployed configuration.

10. A delivery system for deploying an implantable device within a lumen of a body of a patient, the delivery system comprising:
    a delivery device to position an implantable device at a target location within a lumen of a body of a patient, the delivery device transitionable from a delivery configuration to a deployment configuration to deploy the implantable device at the target location, the delivery device including an outer tubular member that, in the delivery configuration, houses the implantable device in a crimped state for delivery to the target location and an inner assembly that is disposed within the outer tubular member, wherein at least one of the inner assembly and the outer tubular member is slidably movable relative to the other; and a panchor disposed at a distal portion of the inner assembly and within a distal portion of the outer tubular member and configured to engage a proximal portion of the implantable device in the crimped state within the outer tubular member in the delivery configuration, wherein the panchor comprise an anchor and a pusher, wherein the panchor comprises a slot to receive and house one or more of (i) ends of a suture coupled to the implantable device, (ii) a knot in the suture, and (iii) a clasp securing the ends of the suture.

11. The delivery system of claim 10, wherein the anchor of the panchor comprises a flange at a distal end of the panchor, the flange configured to be positioned within a proximal portion of a lumen of the implantable device and to engage an inner wall of the implantable device in the crimped state.

12. The delivery system of claim 10, wherein the pusher comprising a push surface facing distally to abut a proximal facing surface of the implantable device in the crimped state and limit proximal movement of the implantable device relative to the pusher during deployment as the delivery device transitions from the delivery configuration to the deployed configuration.

13. The delivery system of claim 6, further comprising a tip disposed at a distal end of the inner assembly, the tip comprising a distal section, a proximal section, and a tip transition zone,
wherein a diameter of a proximal most end of the distal section is greater than a diameter of a distal most end of the proximal section, and
wherein the tip transition zone is a chamfered step to create a smooth transition between the proximal most end of the distal section and the distal most end of the proximal section.

14. The delivery system of claim 6, wherein the inner assembly further comprises an inner sheath positioned inside of the outer tubular member and extending proximally from the panchor, and
wherein the inner sheath comprises a first inner sheath section extending distally from a proximal end to a first inner sheath transition zone and a second inner sheath section extending distally from the first inner sheath transition zone, the first inner sheath section having a first rigidity and the second inner sheath section having a second rigidity that is distinct from the first rigidity.

15. The delivery system of claim 14, wherein the outer tubular member comprises a first outer tubular member section extending distally from a proximal end to a first outer tubular member transition zone and a second outer tubular member section extending distally from the first outer tubular member transition zone, the first outer tubular member section having a third rigidity and the second outer tubular member section having a fourth rigidity that is distinct from the third rigidity.

16. The delivery system of claim 15, wherein the first inner sheath transition zone is offset along the length of the delivery system from the first outer tubular member transition zone.

17. The delivery system of claim 10, further comprising a tip disposed at a distal end of the inner assembly, the tip comprising a distal section, a proximal section, and a tip transition zone,
wherein a diameter of a proximal most end of the distal section is greater than a diameter of a distal most end of the proximal section, and
wherein the tip transition zone is a chamfered step to create a smooth transition between the proximal most end of the distal section and the distal most end of the proximal section.

18. The delivery system of claim 10, wherein the inner assembly further comprises an inner sheath positioned inside of the outer tubular member and extending proximally from the panchor, and
wherein the inner sheath comprises a first inner sheath section extending distally from a proximal end to a first inner sheath transition zone and a second inner sheath section extending distally from the first inner sheath transition zone, the first inner sheath section having a first rigidity and the second inner sheath section having a second rigidity that is distinct from the first rigidity.

19. The delivery system of claim 18, wherein the outer tubular member comprises a first outer tubular member section extending distally from a proximal end to a first outer tubular member transition zone and a second outer tubular member section extending distally from the first outer tubular member transition zone, the first outer tubular member section having a third rigidity and the second outer tubular member section having a fourth rigidity that is distinct from the third rigidity.

20. The delivery system of claim 19, wherein the first inner sheath transition zone is offset along the length of the delivery system from the first outer tubular member transition zone.

* * * * *